United States Patent

Gehring et al.

Patent Number: 4,746,354
Date of Patent: May 24, 1988

[54] 4-NITRO-1-PHENYLPYRAZOLES, COMPOSITION CONTAINING THEM, AND METHOD OF USING THEM TO COMBAT UNWANTED VEGETATION

[75] Inventors: Reinhold Gehring, Wuppertal; Uta Jensen-Korte, Düsseldorf; Otto Schallner, Monheim; Jörg Stetter, Wuppertal; Hans-Joachim Santel, Leverkusen; Robert R. Schmidt, Bergisch Gladbach; Wolfgang Behrenz, Overath, all of Fed. Rep. of Germany

[73] Assignee: Bayer Aktiengesellschaft, Leverkusen, Fed. Rep. of Germany

[21] Appl. No.: 836,268

[22] Filed: Mar. 4, 1986

[30] Foreign Application Priority Data

Mar. 16, 1985 [DE] Fed. Rep. of Germany ....... 3509567

[51] Int. Cl.$^4$ .................... A01N 43/56; C07D 231/16
[52] U.S. Cl. ...................................... 71/92; 548/375; 548/377
[58] Field of Search ..................... 548/375, 377; 71/92

[56] References Cited

U.S. PATENT DOCUMENTS

| 3,869,274 | 3/1975 | Crovetii et al. | 548/375 |
| 4,215,132 | 7/1980 | Maurer et al. | 548/377 |
| 4,459,150 | 7/1984 | Hatton et al. | 548/362 |
| 4,496,390 | 1/1985 | Hatton et al. | 548/362 |

FOREIGN PATENT DOCUMENTS

| 0139182 | 5/1985 | European Pat. Off. | 548/362 |
| 2839270 | 3/1980 | Fed. Rep. of Germany | 548/377 |
| 3226513 | 2/1983 | Fed. Rep. of Germany | . |

OTHER PUBLICATIONS

J. Chem. Soc. B., 1968, 211–214.
J. Heterocycl. Chem. 7, 345–349 (1970).
Farmaco Ed. Sci. 21, 883–891 (1966).
C. A. 66: 115 640p (1967).

*Primary Examiner*—Henry R. Jiles
*Assistant Examiner*—Kurt G. Briscoe
*Attorney, Agent, or Firm*—Sprung Horn Kramer & Woods

[57] ABSTRACT

Herbicidally and insecticidally active 4-nitro-1-phenyl-pyrazoles of the formula

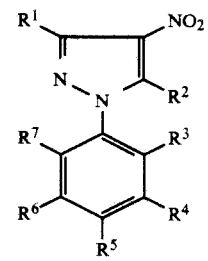

in which
$R^1$ and $R^2$ each independently is hydrogen, alkyl, cycloalkyl, hydroxyalkyl, alkoxyalkyl, alkylthioalkyl or halogenoalkyl,
$R^3$, $R^4$, $R^5$, $R^6$ and $R^7$ each independently is hydrogen, halogen, cyano, nitro, alkyl, alkoxy, alkylthio, alkylsulphinyl, alkylsulphonyl, alkoxycarbonyl, or —(X-)$_n$—$R^8$,
X is oxygen, sulphur, sulphinyl or sulphonyl,
n is 0 or 1, and
$R^8$ is halogenoalkyl.

15 Claims, No Drawings

4-NITRO-1-PHENYLPYRAZOLES, COMPOSITION CONTAINING THEM, AND METHOD OF USING THEM TO COMBAT UNWANTED VEGETATION

The present invention relates to the use of 4-nitro-1-phenyl-pyrazoles, some of which are known, as herbicides and insecticides.

It is already known that certain 5-amino-1-phenyl-pyrazoles which are substituted by a cyano group in the 4-position, such as, for example, 4-cyano-5-propionamido-1-(2,4,6-trichlorophenyl)-pyrazole, have herbicidal properties (compare, for example, DE-OS (German Published Specification) No. 3,226,513).

Their herbicidal activity towards some problem weeds and their tolerance towards important useful plants, however, is not always completely satisfactory in all fields of use.

It is also known that pyrazoles, such as, for example, 5-dimethylaminocarbonyloxy-1-isopropyl-3-methylsulphinylmethylpyrazole or 1-cyclohexyl-5-dimethylaminocarbonyloxy-3-methylthiomethyl-pyrazole have insecticidal properties (compare DE-OS (German Published Specification) No. 2,819,932 and DE-OS (German Published Specification) No. 2,839,270).

However, their action towards all harmful insects is not always completely satisfactory, especially when low amounts or concentrations are applied.

Some 4-nitro-1-phenylpyrazoles, such as, for example, 4-nitro-1-(2,4,6-trinitrophenyl)-pyrazole, 4-nitro-1-(2,4-dichlorophenyl)-pyrazole, 4-nitro-1-pentafluorophenylpyrazole, 3-methyl-4-nitro-1-(2,4-dinitrophenyl)-pyrazole or 3,5-dimethyl-4-nitro-1-(2,4-dinitrophenyl)-pyrazole, are also known [compare, for example, Bull. Soc. Chim. France 1966, 3727–3743; J. Chem. Soc. B., 1968, 211–214; J. Heterocycl. Chem. 7, 345–349 (1970); Farmaco Ed. Sci. 21, 883–891 (1966) and C.A. 66: 115 640 p].

However, nothing is known of a herbicidal or insecticidal activity of these already known compounds.

It has now been found that the 4-nitro-1-phenylpyrazoles, some of which are known, of the general formula (I)

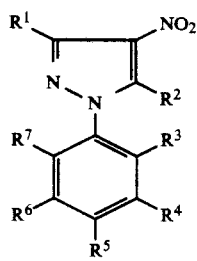

in which
R$^1$ and R$^2$ independently of one another represent hydrogen, alkyl, cycloalkyl, hydroxyalkyl, alkoxyalkyl, alkylthioalkyl or halogenoalkyl and
R$^3$, R$^4$, R$^5$, R$^6$ and R$^7$ each independently of one another represent hydrogen, halogen, cyano, nitro, alkyl, alkoxy, alkylthio, alkylsulphinyl, alkylsulphonyl or alkoxycarbonyl, or represent a radical —(X)$_n$—R$^8$, wherein
X represents oxygen, sulphur, sulphinyl or sulphonyl,
n represents the number 0 or 1 and
R$^8$ represents halogenoalkyl, have herbicidal properties, and in particular selectively herbicidal properties, and moreover also insecticidal properties.

Surprisingly, the 4-nitro-1-phenyl-pyrazoles of the general formula (I) which can be used according to the invention, in addition to having a considerably improved herbicidal activity against harmful plants, also exhibit a clearly improved tolerance towards important crop plants than the 1-phenylpyrazoles known from the prior art, such as, for example, 4-cyano-5-propionamido-1-(2,4,6-trichlorophenyl)-pyrazole, which are closely related compounds chemically and from the point of view of their action. The 4-nitro-1-phenyl-pyrazoles of the formula (I) which can be used according to the invention moreover also show, completely unexpectedly, an insecticidal activity.

Formula (I) provides a general definition of the 4-nitro-1-phenyl-pyrazoles which can be used according to the invention. Preferred compounds of the formula (I) are those in which
R$^1$ and R$^2$ each independently of one another represent hydrogen, or represent in each case straight-chain or branched alkyl, hydroxyalkyl, alkoxyalkyl, alkylthioalkyl or halogenoalkyl with in each case up to 4 carbon atoms in the individual alkyl parts and, where appropriate, up to 9 identical or different halogen atoms, or represent cycloalkyl with 3 to 7 carbon atoms and
R$^3$, R$^4$, R$^5$, R$^6$ and R$^7$ each independently of one another represent hydrogen, fluorine, chlorine, bromine, iodine, cyano, nitro or in each case straight-chain or branched alkyl, alkoxy, alkylthio, alkylsulphinyl, alkylsulphonyl or alkoxycarbonyl with in each case up to 4 carbon atoms in the individual alkyl parts, or represent a radical —(X)$_n$—R$^8$, wherein
X represents oxygen, sulphur, sulphinyl or sulphonyl,
n represents the number 0 or 1 and
R$^8$ represents straight-chain or branched halogenoalkyl with up to 4 carbon atoms and up to 9 identical or different halogen atoms.

Compounds of the formula (I) which are particularly preferably used are those in which
R$^1$ and R$^2$ independently of one another represent hydrogen, methyl, ethyl, n- or i-propyl, n-, i-, s- or t-butyl, cyclohexyl, hydroxymethyl, methoxymethyl, methylthiomethyl, trifluoromethyl or trichloromethyl and
R$^3$, R$^4$, R$^5$, R$^6$ and R$^7$ each independently of one another represent hydrogen, fluorine, chlorine, bromine, iodine, cyano, nitro, methyl, ethyl, n- or i-propyl, methoxy, ethoxy, methylthio, methylsulphinyl, methylsulphonyl, methoxycarbonyl or ethoxycarbonyl, or represent a radical —(X)$_n$—R$^8$, wherein
X represents oxygen, sulphur, sulphinyl or sulphonyl,
n represents 0 or 1 and
R$^8$ represents trifluoromethyl, trichloromethyl, dichlorofluoromethyl, difluorochloromethyl, dichloromethyl, chloromethyl, difluoromethyl, pentafluoroethyl, tetrafluoroethyl, trifluorochloroethyl, trifluoroethyl, difluorodichloroethyl, trifluorodichloroethyl or pentachloroethyl.

The following compounds of the general formula (I) may be mentioned specifically, in addition to the compounds mentioned in the preparation examples:

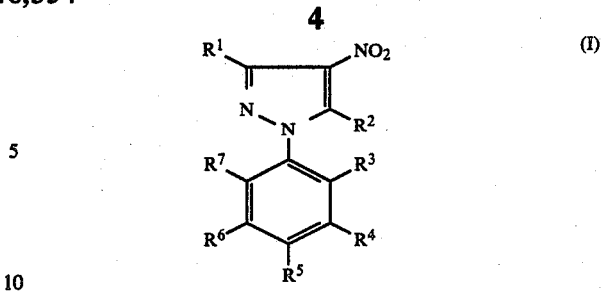

(I)

TABLE 1

| R¹ | R² | R³ | R⁴ | R⁵ | R⁶ | R⁷ |
|---|---|---|---|---|---|---|
| H | H | H | H | CF₃ | H | H |
| H | H | Cl | H | CF₃ | H | H |
| H | H | Cl | H | CF₃ | H | Cl |
| H | H | Cl | Cl | CF₃ | H | Cl |
| H | H | F | H | CF₃ | H | H |
| H | H | F | H | CF₃ | H | F |
| H | H | F | F | CF₃ | F | F |
| H | H | Cl | Cl | CF₃ | H | H |
| H | H | Cl | F | CF₃ | F | Cl |
| H | H | Cl | F | CF₃ | F | F |
| H | H | F | F | CN | F | F |
| H | H | Cl | H | Br | H | Cl |
| H | H | Cl | F | CN | F | F |
| H | H | Cl | F | CN | F | Cl |
| CH₃ | H | Cl | F | CF₃ | F | Cl |
| CH₃ | H | Cl | F | CF₃ | F | F |
| CH₃ | H | F | F | CN | F | F |
| CH₃ | H | Cl | F | CN | F | F |
| CH₃ | H | Cl | F | CN | F | Cl |
| CH₃ | H | Cl | H | Br | H | Cl |
| H | CH₃ | Cl | F | CF₃ | F | Cl |
| H | CH₃ | Cl | F | CF₃ | F | F |
| H | CH₃ | F | F | CN | F | F |
| H | CH₃ | Cl | F | CN | F | F |
| H | CH₃ | Cl | F | CN | F | Cl |
| H | CH₃ | Cl | H | Br | H | Cl |
| CH₃ | CH₃ | Cl | F | CF₃ | F | Cl |
| CH₃ | CH₃ | Cl | F | CF₃ | F | F |
| CH₃ | CH₃ | F | F | CN | F | F |
| CH₃ | CH₃ | Cl | F | CN | F | F |
| CH₃ | CH₃ | Cl | F | CN | F | Cl |
| CH₃ | CH₃ | Cl | H | Br | H | Cl |
| H | H | Cl | H | CF₃ | H | F |
| H | H | Br | H | CF₃ | H | H |
| H | H | Br | H | CF₃ | H | Br |
| CH₃ | H | H | H | CF₃ | H | H |
| CH₃ | H | Cl | H | CF₃ | H | H |
| CH₃ | H | Cl | H | CF₃ | H | Cl |
| CH₃ | H | Cl | Cl | CF₃ | H | Cl |
| CH₃ | H | F | H | CF₃ | H | H |
| CH₃ | H | F | H | CF₃ | H | F |
| CH₃ | H | F | F | CF₃ | F | F |
| CH₃ | H | Cl | Cl | CF₃ | H | H |
| CH₃ | H | Cl | H | CF₃ | H | F |
| CH₃ | H | Br | Br | CF₃ | H | H |
| CH₃ | H | Br | Br | CF₃ | H | Br |
| CH₃ | CH₃ | H | H | CF₃ | H | H |
| CH₃ | CH₃ | Cl | H | CF₃ | H | H |
| CH₃ | CH₃ | Cl | H | CF₃ | H | Cl |
| CH₃ | CH₃ | Cl | Cl | CF₃ | H | Cl |
| CH₃ | CH₃ | F | H | CF₃ | H | H |
| CH₃ | CH₃ | F | H | CF₃ | H | F |
| CH₃ | CH₃ | F | F | CF₃ | F | F |
| CH₃ | CH₃ | Cl | Cl | CF₃ | H | H |
| CH₃ | CH₃ | Cl | H | CF₃ | H | F |
| CH₃ | CH₃ | Br | H | CF₃ | H | Br |
| H | CH₃ | H | H | CF₃ | H | H |
| H | CH₃ | Cl | H | CF₃ | H | H |
| H | CH₃ | Cl | H | CF₃ | H | Cl |
| H | CH₃ | Cl | Cl | CF₃ | H | Cl |
| H | CH₃ | F | H | CF₃ | H | H |
| H | CH₃ | F | H | CF₃ | H | F |
| H | CH₃ | F | F | CF₃ | F | F |
| H | CH₃ | Cl | Cl | CF₃ | H | H |
| H | H | Cl | H | CF₃ | H | F |
| H | CH₃ | Br | H | CF₃ | H | H |
| H | CH₃ | Br | H | CF₃ | H | Br |

TABLE 1-continued

| R¹ | R² | R³ | R⁴ | R⁵ | R⁶ | R⁷ |
|---|---|---|---|---|---|---|
| H | H | F | H | OCF₃ | H | H |
| H | H | F | H | OCF₃ | H | F |
| H | H | F | F | OCF₃ | F | F |
| H | H | Cl | H | OCF₃ | H | H |
| H | H | Cl | H | OCF₃ | H | Cl |
| H | H | Cl | Cl | OCF₃ | H | H |
| H | H | Cl | Cl | OCF₃ | H | Cl |
| H | H | Br | H | OCF₃ | H | H |
| H | H | Br | H | OCF₃ | H | Br |
| H | CH₃ | F | H | OCF₃ | H | H |
| H | CH₃ | F | H | OCF₃ | H | F |
| H | CH₃ | F | F | OCF₃ | F | F |
| H | CH₃ | Cl | H | OCF₃ | H | H |
| H | CH₃ | Cl | H | OCF₃ | H | Cl |
| H | CH₃ | Cl | Cl | OCF₃ | H | H |
| H | CH₃ | Cl | Cl | OCF₃ | H | Cl |
| H | CH₃ | Br | H | OCF₃ | H | H |
| H | CH₃ | Br | H | OCF₃ | H | Br |
| CH₃ | H | F | H | OCF₃ | H | H |
| CH₃ | H | F | H | OCF₃ | H | F |
| CH₃ | H | F | F | OCF₃ | F | F |
| CH₃ | H | Cl | H | OCF₃ | H | H |
| CH₃ | H | Cl | H | OCF₃ | H | Cl |
| CH₃ | H | Cl | Cl | OCF₃ | H | H |
| CH₃ | H | Cl | Cl | OCF₃ | H | Cl |
| CH₃ | H | Br | H | OCF₃ | H | H |
| CH₃ | H | Br | H | OCF₃ | H | Br |
| CH₃ | CH₃ | F | H | OCF₃ | H | H |
| CH₃ | CH₃ | F | H | OCF₃ | H | F |
| CH₃ | CH₃ | F | F | OCF₃ | F | F |
| CH₃ | CH₃ | Cl | H | OCF₃ | H | H |
| CH₃ | CH₃ | Cl | H | OCF₃ | H | Cl |
| CH₃ | CH₃ | Cl | Cl | OCF₃ | H | H |
| CH₃ | CH₃ | Cl | Cl | OCF₃ | H | Cl |
| CH₃ | CH₃ | Br | H | OCF₃ | H | H |
| CH₃ | CH₃ | Br | H | OCF₃ | H | Br |
| H | CH₃ | Cl | H | —S—CH₂CF₃ | H | H |
| H | CH₃ | Cl | H | —S—CH₂CF₃ | H | Cl |
| H | CH₃ | Br | H | —S—CH₂CF₃ | H | H |
| H | CH₃ | Br | H | —S—CH₂CF₃ | H | Br |
| H | CH₃ | Cl | Cl | —S—CH₂CF₃ | H | H |
| CH₃ | H | Cl | H | —S—CH₂CF₃ | H | H |
| CH₃ | CH₃ | Cl | H | —S—CH₂CF₃ | H | Cl |
| CH₃ | CH₃ | Br | H | —S—CH₂CF₃ | H | H |
| CH₃ | CH₃ | Br | H | —S—CH₂CF₃ | H | Br |
| CH₃ | CH₃ | Cl | Cl | —S—CH₂CF₃ | H | H |
| H | CH₃ | Cl | H | —S—CH₂CF₃ | H | H |
| H | CH₃ | Cl | H | —S—CH₂CF₃ | H | Cl |
| H | CH₃ | Br | H | —S—CH₂CF₃ | H | H |
| H | CH₃ | Br | H | —S—CH₂CF₃ | H | Br |
| H | CH₃ | Cl | Cl | —S—CH₂CF₃ | H | H |
| CH₃ | CH₃ | Cl | H | —S—CH₂CF₃ | H | H |
| CH₃ | CH₃ | Cl | H | —S—CH₂CF₃ | H | Cl |
| CH₃ | CH₃ | Br | H | —S—CH₂CF₃ | H | H |
| CH₃ | CH₃ | Br | H | —S—CH₂CF₃ | H | Br |
| CH₃ | CH₃ | Cl | Cl | —S—CH₂CF₃ | H | H |
| H | CH₃ | Cl | H | —O—CH₂CF₃ | H | H |
| H | CH₃ | Cl | H | —O—CH₂CF₃ | H | Cl |
| H | CH₃ | Br | H | —O—CH₂CF₃ | H | H |
| H | CH₃ | Br | H | —O—CH₂CF₃ | H | Br |
| H | H | Cl | H | —O—CH₂CF₃ | H | H |
| H | H | Cl | H | —O—CH₂CF₃ | H | Cl |
| H | H | Br | H | —O—CH₂CF₃ | H | H |
| H | H | Br | H | —O—CH₂CF₃ | H | Br |
| CH₃ | H | Cl | H | —O—CH₂CF₃ | H | H |
| CH₃ | H | Cl | H | —O—CH₂CF₃ | H | Cl |
| CH₃ | H | Br | H | —O—CH₂CF₃ | H | H |
| CH₃ | H | Br | H | —O—CH₂CF₃ | H | Br |
| CH₃ | CH₃ | Cl | H | —O—CH₂CF₃ | H | H |
| CH₃ | CH₃ | Cl | H | —O—CH₂CF₃ | H | Cl |
| CH₃ | CH₃ | Br | H | —O—CH₂CF₃ | H | H |
| CH₃ | CH₃ | Br | H | —O—CH₂CF₃ | H | Br |
| H | H | SCF₃ | H | Cl | H | H |
| H | CH₃ | SCF₃ | H | Cl | H | H |
| H | H | SCF₃ | H | Cl | H | Cl |
| H | CH₃ | SCF₃ | H | Cl | H | Cl |
| H | H | F | H | SCF₃ | H | H |
| H | H | F | H | SCF₃ | H | F |
| H | H | F | F | SCF₃ | F | F |
| H | H | Cl | H | SCF₃ | H | H |
| H | H | Cl | H | SCF₃ | H | Cl |

TABLE 1-continued

| R¹ | R² | R³ | R⁴ | R⁵ | R⁶ | R⁷ |
|---|---|---|---|---|---|---|
| H | H | Cl | Cl | SCF₃ | H | H |
| H | H | Cl | Cl | SCF₃ | H | Cl |
| H | H | Br | H | SCF₃ | H | H |
| H | H | Br | H | SCF₃ | H | Br |
| H | CH₃ | F | H | SCF₃ | H | H |
| H | CH₃ | F | H | SCF₃ | H | F |
| H | CH₃ | F | F | SCF₃ | F | F |
| H | CH₃ | Cl | H | SCF₃ | H | H |
| H | CH₃ | Cl | H | SCF₃ | H | Cl |
| H | CH₃ | Cl | Cl | SCF₃ | H | H |
| H | CH₃ | Cl | Cl | SCF₃ | H | Cl |
| H | CH₃ | Br | H | SCF₃ | H | H |
| H | CH₃ | Br | H | SCF₃ | H | Br |
| CH₃ | H | F | H | SCF₃ | H | H |
| CH₃ | H | F | H | SCF₃ | H | F |
| CH₃ | H | F | H | SCF₃ | F | F |
| CH₃ | H | Cl | H | SCF₃ | H | H |
| CH₃ | H | Cl | H | SCF₃ | H | Cl |
| CH₃ | H | Cl | H | SCF₃ | H | F |
| CH₃ | H | Br | H | SCF₃ | H | H |
| CH₃ | CH₃ | F | H | SCF₃ | H | H |
| CH₃ | CH₃ | F | H | SCF₃ | H | F |
| CH₃ | CH₃ | F | F | SCF₃ | F | F |
| CH₃ | CH₃ | Cl | H | SCF₃ | H | H |
| CH₃ | CH₃ | Cl | H | SCF₃ | H | Cl |
| CH₃ | CH₃ | Cl | Cl | SCF₃ | H | H |
| CH₃ | CH₃ | Cl | Cl | SCF₃ | H | Cl |
| CH₃ | CH₃ | Br | H | SCF₃ | H | H |
| CH₃ | CH₃ | Br | H | SCF₃ | H | Br |
| H | H | CF₃ | H | —SO₂CH₃ | H | H |
| H | H | CF₃ | H | —SCF₃ | H | H |
| H | H | OCF₃ | H | CF₃ | H | H |
| H | H | OCF₃ | H | —OCF₃ | H | H |
| H | CH₃ | CF₃ | H | —SO₂CH₃ | H | H |
| H | CH₃ | CF₃ | H | —SO₂CH₃ | H | H |
| H | CH₃ | CF₃ | H | —SCF₃ | H | H |
| H | CH₃ | OCF₃ | H | —OCF₃ | H | H |
| H | CH₃ | OCF₃ | H | —CF₃ | H | H |
| CH₃ | H | CF₃ | H | —SO₂CH₃ | H | H |
| CH₃ | H | CF₃ | H | —SO₂CH₃ | H | H |
| CH₃ | H | CF₃ | H | —SCF₃ | H | H |
| CH₃ | H | OCF₃ | H | —OCF₃ | H | H |
| CH₃ | H | OCF₃ | H | —CF₃ | H | H |
| CH₃ | CH₃ | CF₃ | H | —SO₂CH₃ | H | H |
| CH₃ | CH₃ | CF₃ | H | —SO₂CH₃ | H | H |
| CH₃ | CH₃ | CF₃ | H | —SCF₃ | H | H |
| CH₃ | CH₃ | OCF₃ | H | —OCF₃ | H | H |
| CH₃ | CH₃ | OCF₃ | H | —CF₃ | H | H |
| H | H | Cl | H | —SCHF₂ | H | H |
| H | H | Cl | H | —SCHF₂ | H | Cl |
| H | H | Br | H | —SCHF₂ | H | H |
| H | H | Br | H | —SCHF₂ | H | Br |
| H | CH₃ | Cl | H | —SCHF₂ | H | H |
| H | CH₃ | Cl | H | —SCHF₂ | H | Cl |
| H | CH₃ | Br | H | —SCHF₂ | H | H |
| H | CH₃ | Br | H | —SCHF₂ | H | Br |
| H | H | Cl | H | —SCHF₂ | H | H |
| H | H | Cl | H | —SCHF₂ | H | Cl |
| H | H | Br | H | —SCHF₂ | H | H |
| H | H | Br | H | —SCHF₂ | H | Br |
| CH₃ | H | Cl | H | —SCHF₂ | H | H |
| CH₃ | H | Cl | H | —SCHF₂ | H | Cl |
| CH₃ | H | Br | H | —SCHF₂ | H | H |
| CH₃ | H | Br | H | —SCHF₂ | H | Br |
| H | H | Cl | H | —SCF₂CHF₂ | H | H |
| H | H | Cl | H | —SCF₂CHF₂ | H | Cl |
| H | H | Br | H | —SCF₂CHF₂ | H | H |
| H | H | Br | H | —SCF₂CHF₂ | H | Br |
| H | CH₃ | Cl | H | —SCF₂CHF₃ | H | H |
| H | CH₃ | Cl | H | —SCF₂CHF₂ | H | Cl |
| H | CH₃ | Br | H | —SCF₂CHF₂ | H | H |
| H | CH₃ | Br | H | —SCF₂CHF₂ | H | Br |
| CH₃ | H | Cl | H | —SCF₂CHF₂ | H | H |
| CH₃ | H | Cl | H | —SCF₂CHF₂ | H | Cl |
| CH₃ | H | Br | H | —SCF₂CHF₂ | H | H |
| CH₃ | H | Br | H | —SCF₂CHF₂ | H | Br |
| CH₃ | CH₃ | Cl | H | —SCF₂CHF₂ | H | H |
| CH₃ | CH₃ | Cl | H | —SCF₂CHF₂ | H | Cl |
| CH₃ | CH₃ | Br | H | —SCF₂CHF₂ | H | H |
| CH₃ | CH₃ | Br | H | —SCF₂CHF₂ | H | Br |
| H | H | Cl | H | —SCF₂CHFCl | H | H |

TABLE 1-continued

| R¹ | R² | R³ | R⁴ | R⁵ | R⁶ | R⁷ |
|---|---|---|---|---|---|---|
| H | H | Cl | H | —SCF₂CHFCl | H | Cl |
| H | H | Br | H | —SCF₂CHFCl | H | H |
| H | H | Br | H | —SCF₂CHFCl | H | Br |
| H | CH₃ | Cl | H | —SCF₂CHFCl | H | H |
| H | CH₃ | Cl | H | —SCF₂CHFCl | H | Cl |
| H | CH₃ | Br | H | —SCF₂CHFCl | H | H |
| H | CH₃ | Br | H | —SCF₂CHFCl | H | Br |
| CH₃ | H | Cl | H | —SCF₂CHFCl | H | H |
| CH₃ | H | Cl | H | —SCF₂CHFCl | H | Cl |
| CH₃ | H | Cl | H | —SCF₂CHFCl | H | Cl |
| CH₃ | H | Br | H | —SCF₂CHFCl | H | H |
| CH₃ | H | Br | H | —SCF₂CHFCl | H | Br |
| CH₃ | CH₃ | Cl | H | —SCF₂CHFCl | H | H |
| CH₃ | CH₃ | Cl | H | —SCF₂CHFCl | H | Cl |
| CH₃ | CH₃ | Br | H | —SCF₂CHFCl | H | H |
| CH₃ | CH₃ | Br | H | —SCF₂CHFCl | H | Br |
| C₂H₅ | H | Cl | H | —SCF₃ | H | H |
| C₂H₅ | H | Cl | H | —OCF₃ | H | Cl |
| C₂H₅ | H | Br | H | —OCF₃ | H | H |
| C₂H₅ | H | Br | H | —OCF₃ | H | Br |
| C₂H₅ | CH₃ | Cl | H | —OCF₃ | H | H |
| C₂H₅ | CH₃ | Cl | H | —OCF₃ | H | Cl |
| C₂H₅ | H | Cl | H | —SCF₃ | H | H |
| C₂H₅ | H | Cl | H | —SCF₃ | H | Cl |
| C₂H₅ | H | Br | H | —SCF₃ | H | H |
| H | H | Cl | H | —SOCF₃ | H | H |
| H | H | Cl | H | —SOCF₃ | H | Cl |
| H | H | Br | H | —SOCF₃ | H | Br |
| H | H | Br | H | —SOCF₃ | H | H |
| H | H | CF₃ | H | —SOCF₃ | H | H |
| H | H | CF₃ | H | —SOCF₃ | H | Cl |
| H | CH₃ | Cl | H | —SOCF₃ | H | H |
| H | CH₃ | Cl | H | —SOCF₃ | H | Cl |
| H | CH₃ | Br | H | —SOCF₃ | H | Br |
| H | CH₃ | Br | H | —SOCF₃ | H | H |
| H | CH₃ | CF₃ | H | —SOCF₃ | H | H |
| H | CH₃ | CF₃ | H | —SOCF₃ | H | Cl |
| CH₃ | H | Cl | H | —SOCF₃ | H | H |
| CH₃ | H | Cl | H | —SOCF₃ | H | Cl |
| CH₃ | H | Br | H | —SOCF₃ | H | Br |
| CH₃ | H | Br | H | —SOCF₃ | H | H |
| CH₃ | H | CF₃ | H | —SOCF₃ | H | H |
| CH₃ | H | CF₃ | H | —SOCF₃ | H | Cl |
| CH₃ | CH₃ | Cl | H | —SOCF₃ | H | H |
| CH₃ | CH₃ | Cl | H | —SOCF₃ | H | Cl |
| CH₃ | CH₃ | Br | H | —SOCF₃ | H | Br |
| CH₃ | CH₃ | Br | H | —SOCF₃ | H | H |
| CH₃ | CH₃ | CF₃ | H | —SOCF₃ | H | H |
| CH₃ | CH₃ | CF₃ | H | —SOCF₃ | H | Cl |
| H | H | Cl | H | —OCF₂CHFCl | H | H |
| H | H | Cl | H | —OCF₂CHFCl | H | Cl |
| H | H | Br | H | —OCF₂CHFCl | H | H |
| H | CH₃ | Cl | H | —OCF₂CHFCl | H | Br |
| H | CH₃ | Cl | H | —OCF₂CHFCl | H | H |
| H | H | Cl | H | —OCF₂CHFCl | H | Cl |
| H | H | Br | H | —OCF₂CHFCl | H | H |
| H | H | Br | H | —OCF₂CHFCl | H | Br |
| CH₃ | H | Cl | H | —OCF₂CHFCl | H | H |
| CH₃ | H | Cl | H | —OCF₂CHFCl | H | Cl |
| CH₃ | H | Br | H | —OCF₂CHFCl | H | H |
| CH₃ | H | Br | H | —OCF₂CHFCl | H | Br |
| CH₃ | CH₃ | Cl | H | —OCF₂CHFCl | H | H |
| CH₃ | CH₃ | Cl | H | —OCF₂CHFCl | H | Cl |
| CH₃ | CH₃ | Br | H | —OCF₂CHFCl | H | H |
| CH₃ | CH₃ | Br | H | —OCF₂CHFCl | H | Br |
| H | H | Cl | H | —OCF₂CHCl₂ | H | H |
| H | H | Cl | H | —OCF₂CHCl₂ | H | Cl |
| H | H | Br | H | —OCF₂CHCl₂ | H | H |
| H | H | Br | H | —OCF₂CHCl₂ | H | Br |
| H | CH₃ | Cl | H | —OCF₂CHCl₂ | H | H |
| H | CH₃ | Cl | H | —OCF₂CHCl₂ | H | Cl |
| H | CH₃ | Br | H | —OCF₂CHCl₂ | H | H |
| H | CH₃ | Br | H | —OCF₂CHCl₂ | H | Br |
| CH₃ | H | Cl | H | —OCF₂CHCl₂ | H | H |
| CH₃ | H | Cl | H | —OCF₂CHCl₂ | H | Cl |
| CH₃ | H | Br | H | —OCF₂CHCl₂ | H | H |
| CH₃ | H | Br | H | —OCF₂CHCl₂ | H | Br |
| CH₃ | CH₃ | Cl | H | —OCF₂CHCl₂ | H | H |
| CH₃ | CH₃ | Cl | H | —OCF₂CHCl₂ | H | Cl |
| CH₃ | CH₃ | Br | H | —OCF₂CHCl₂ | H | H |
| CH₃ | CH₃ | Br | H | —OCF₂CHCl₂ | H | Br |

TABLE 1-continued

| R¹ | R² | R³ | R⁴ | R⁵ | R⁶ | R⁷ |
|---|---|---|---|---|---|---|
| H | H | Cl | H | —OCF$_2$CHF$_2$ | H | H |
| H | H | Cl | H | —OCF$_2$CHF$_2$ | H | Cl |
| H | H | Br | H | —OCF$_2$CHF$_2$ | H | H |
| H | H | Br | H | —OCF$_2$CHF$_2$ | H | Br |
| H | CH$_3$ | Cl | H | —OCF$_2$CHF$_2$ | H | H |
| H | CH$_3$ | Cl | H | —OCF$_2$CHF$_2$ | H | Cl |
| H | CH$_3$ | Br | H | —OCF$_2$CHF$_2$ | H | H |
| H | CH$_3$ | Br | H | —OCF$_2$CHF$_2$ | H | Br |
| CH$_3$ | H | Cl | H | —OCF$_2$CHF$_2$ | H | H |
| CH$_3$ | H | Cl | H | —OCF$_2$CHF$_2$ | H | Cl |
| CH$_3$ | H | Br | H | —OCF$_2$CHF$_2$ | H | H |
| CH$_3$ | H | Br | H | —OCF$_2$CHF$_2$ | H | Br |
| CH$_3$ | CH$_3$ | Cl | H | —OCF$_2$CHF$_2$ | H | H |
| CH$_3$ | CH$_3$ | Cl | H | —OCF$_2$CHF$_2$ | H | Cl |
| CH$_3$ | CH$_3$ | Br | H | —OCF$_2$CHF$_2$ | H | H |
| CH$_3$ | CH$_3$ | Br | H | —OCF$_2$CHF$_2$ | H | Br |
| H | H | Cl | H | —SO$_2$CF$_3$ | H | H |
| H | H | Cl | H | —SO$_2$CF$_3$ | H | Cl |
| H | H | Br | H | —SO$_2$CF$_3$ | H | H |
| H | H | Br | H | —SO$_2$CF$_3$ | H | Br |
| H | H | CF$_3$ | H | —SO$_2$CF$_3$ | H | H |
| H | CH$_3$ | Cl | H | —SO$_2$CF$_3$ | H | H |
| H | CH$_3$ | Cl | H | —SO$_2$CF$_3$ | H | Cl |
| H | CH$_3$ | Br | H | —SO$_2$CF$_3$ | H | H |
| H | CH$_3$ | Br | H | —SO$_2$CF$_3$ | H | Br |
| H | CH$_3$ | CF$_3$ | H | —SO$_2$CF$_3$ | H | H |
| CH$_3$ | H | Cl | H | —SO$_2$CF$_3$ | H | H |
| CH$_3$ | H | Cl | H | —SO$_2$CF$_3$ | H | Cl |
| CH$_3$ | H | Br | H | —SO$_2$CF$_3$ | H | H |
| CH$_3$ | H | Br | H | —SO$_2$CF$_3$ | H | Br |
| CH$_3$ | H | CF$_3$ | H | —SO$_2$CF$_3$ | H | H |
| CH$_3$ | CH$_3$ | Cl | H | —SO$_2$CF$_3$ | H | H |
| CH$_3$ | CH$_3$ | Cl | H | —SO$_2$CF$_3$ | H | Cl |
| CH$_3$ | CH$_3$ | Br | H | —SO$_2$CF$_3$ | H | H |
| CH$_3$ | CH$_3$ | Br | H | —SO$_2$CF$_3$ | H | Br |
| CH$_3$ | CH$_3$ | CF$_3$ | H | —SO$_2$CF$_3$ | H | H |
| H | H | F | H | —SCCl$_2$F | H | H |
| H | H | F | H | —SCCl$_2$F | H | F |
| H | H | F | H | —SCCl$_2$F | F | F |
| H | H | Cl | H | —SCCl$_2$F | H | H |
| H | H | Cl | H | —SCCl$_2$F | H | Cl |
| H | H | Cl | Cl | —SCCl$_2$F | H | Cl |
| H | H | Br | H | —SCCl$_2$F | H | H |
| H | H | Br | H | —SCCl$_2$F | H | Br |
| H | CH$_3$ | F | H | —SCCl$_2$F | H | H |
| H | CH$_3$ | F | H | —SCCl$_2$F | H | F |
| H | CH$_3$ | F | F | —SCCl$_2$F | F | F |
| H | CH$_3$ | Cl | H | —SCCl$_2$F | H | H |
| H | CH$_3$ | Cl | H | —SCCl$_2$F | H | Cl |
| H | CH$_3$ | Cl | Cl | —SCCl$_2$F | H | Cl |
| H | CH$_3$ | Br | H | —SCCl$_2$F | H | H |
| H | CH$_3$ | Br | H | —SCCl$_2$F | H | Br |
| CH$_3$ | H | F | H | —SCCl$_2$F | H | H |
| CH$_3$ | H | F | H | —SCCl$_2$F | H | F |
| CH$_3$ | H | F | H | —SCCl$_2$F | F | F |
| CH$_3$ | H | Cl | H | —SCCl$_2$F | H | H |
| CH$_3$ | H | Cl | H | —SCCl$_2$F | H | Cl |
| CH$_3$ | H | Cl | Cl | —SCCl$_2$F | H | Cl |
| CH$_3$ | H | Br | H | —SCCl$_2$F | H | H |
| CH$_3$ | H | Br | H | —SCCl$_2$F | H | Br |
| CH$_3$ | CH$_3$ | F | H | —SCCl$_2$F | H | H |
| CH$_3$ | CH$_3$ | F | H | —SCCl$_2$F | H | F |
| CH$_3$ | CH$_3$ | F | F | —SCCl$_2$F | F | F |
| CH$_3$ | CH$_3$ | Cl | H | —SCCl$_2$F | H | H |
| CH$_3$ | CH$_3$ | Cl | H | —SCCl$_2$F | H | Cl |
| CH$_3$ | CH$_3$ | Cl | Cl | —SCCl$_2$F | H | Cl |
| CH$_3$ | CH$_3$ | Br | H | —SCCl$_2$F | H | H |
| CH$_3$ | CH$_3$ | Br | H | —SCCl$_2$F | H | Br |
| H | H | F | H | —OCHF$_2$ | H | H |
| H | H | F | H | —OCHF$_2$ | H | F |
| H | H | F | F | —OCHF$_2$ | F | F |
| H | H | Cl | H | —OCHF$_2$ | H | H |
| H | H | Cl | H | —OCHF$_2$ | H | Cl |
| H | H | Cl | Cl | —OCHF$_2$ | H | Cl |
| H | H | Br | H | —OCHF$_2$ | H | H |
| H | H | Br | H | —OCHF$_2$ | H | Br |
| H | CH$_3$ | F | H | —OCHF$_2$ | H | H |
| H | CH$_3$ | F | H | —OCHF$_2$ | H | F |
| H | CH$_3$ | F | F | —OCHF$_2$ | F | F |
| H | CH$_3$ | Cl | H | —OCHF$_2$ | H | H |
| H | CH$_3$ | Cl | H | —OCHF$_2$ | H | Cl |

TABLE 1-continued

| R¹ | R² | R³ | R⁴ | R⁵ | R⁶ | R⁷ |
|---|---|---|---|---|---|---|
| H | CH₃ | Cl | Cl | —OCHF₂ | H | Cl |
| H | CH₃ | Br | H | —OCHF₂ | H | H |
| H | CH₃ | Br | H | —OCHF₂ | H | Br |
| CH₃ | H | F | H | —OCHF₂ | H | H |
| CH₃ | H | F | H | —OCHF₂ | H | F |
| CH₃ | H | F | F | —OCHF₂ | F | F |
| CH₃ | H | Cl | H | —OCHF₂ | H | H |
| CH₃ | H | Cl | H | —OCHF₂ | H | Cl |
| CH₃ | H | Cl | Cl | —OCHF₂ | H | Cl |
| CH₃ | H | Br | H | —OCHF₂ | H | H |
| CH₃ | H | Br | H | —OCHF₂ | H | Br |
| CH₃ | CH₃ | F | H | —OCHF₂ | H | H |
| CH₃ | CH₃ | F | H | —OCHF₂ | H | F |
| CH₃ | CH₃ | F | F | —OCHF₂ | F | F |
| CH₃ | CH₃ | Cl | H | —OCHF₂ | H | H |
| CH₃ | CH₃ | Cl | H | —OCHF₂ | H | Cl |
| CH₃ | CH₃ | Cl | Cl | —OCHF₂ | H | F |
| CH₃ | CH₃ | Br | H | —OCHF₂ | H | H |
| CH₃ | CH₃ | Br | H | —OCHF₂ | H | Br |
| C₂H₅ | H | Cl | H | CF₃ | H | Cl |
| C₂H₅ | H | Cl | Cl | CF₃ | H | Cl |
| C₂H₅ | H | Cl | H | CF₃ | H | H |
| C₂H₅ | H | Cl | H | OCF₃ | H | H |
| C₂H₅ | H | Cl | H | SOCF₃ | H | H |
| C₂H₅ | H | Cl | H | SOCF₃ | H | Cl |
| C₂H₅ | H | Cl | H | SO₂CF₃ | H | H |
| C₂H₅ | H | Cl | H | SO₂CF₃ | H | Cl |
| C₂H₅ | H | Cl | H | Br | H | Cl |
| C₂H₅ | C₂H₅ | Cl | H | CF₃ | H | Cl |
| C₂H₅ | C₂H₅ | Cl | Cl | CF₃ | H | Cl |
| C₂H₅ | C₂H₅ | Cl | H | OCF₃ | H | H |
| C₂H₅ | C₂H₅ | Cl | H | OCF₃ | H | H |
| C₂H₅ | C₂H₅ | Cl | H | OCF₃ | H | Cl |
| C₂H₅ | C₂H₅ | Cl | H | SCF₃ | H | H |
| C₂H₅ | C₂H₅ | Cl | H | SCF₃ | H | Cl |
| C₂H₅ | C₂H₅ | Cl | H | SOCF₃ | H | H |
| C₂H₅ | C₂H₅ | Cl | H | SOCF₃ | H | Cl |
| C₂H₅ | C₂H₅ | Cl | H | SO₂CF₃ | H | H |
| C₂H₅ | C₂H₅ | Cl | H | SO₂CF₃ | H | Cl |
| C₂H₅ | C₂H₅ | Cl | H | Br | H | Cl |
| i-C₃H₇ | H | Cl | H | CF₃ | H | Cl |
| i-C₃H₇ | H | Cl | Cl | CF₃ | H | Cl |
| i-C₃H₇ | H | Cl | H | CF₃ | H | H |
| i-C₃H₇ | H | Cl | H | OCF₃ | H | H |
| i-C₃H₇ | H | Cl | H | OCF₃ | H | Cl |
| i-C₃H₇ | H | Cl | H | SCF₃ | H | H |
| i-C₃H₇ | H | Cl | H | SCF₃ | H | Cl |
| i-C₃H₇ | H | Cl | H | SOCF₃ | H | H |
| i-C₃H₇ | H | Cl | H | SOCF₃ | H | Cl |
| i-C₃H₇ | H | Cl | H | SO₂CF₃ | H | H |
| i-C₃H₇ | H | Cl | H | SO₂₂CF₃ | H | Cl |
| i-C₃H₇ | H | Cl | H | Br | H | Cl |
| i-C₃H₇ | H | Cl | H | CF₃ | H | Cl |
| i-C₃H₇ | H | Cl | Cl | CF₃ | H | Cl |
| i-C₃H₇ | H | Cl | H | CF₃ | H | H |
| i-C₃H₇ | H | Cl | H | OCF₃ | H | H |
| i-C₃H₇ | H | Cl | H | OCF₃ | H | Cl |
| i-C₃H₇ | H | Cl | H | SCF₃ | H | H |
| i-C₃H₇ | H | Cl | H | SCF₃ | H | Cl |
| i-C₃H₇ | H | Cl | H | SOCF₃ | H | H |
| i-C₃H₇ | H | Cl | H | SOCF₃ | H | Cl |
| i-C₃H₇ | H | Cl | H | SO₂CF₃ | H | H |
| i-C₃H₇ | H | Cl | H | SO₂CF₃ | H | Cl |
| i-C₃H₇ | H | Cl | H | Br | H | Cl |
| i-C₃H₇ | i-C₃H₇ | Cl | H | CF₃ | H | Cl |
| i-C₃H₇ | i-C₃H₇ | Cl | Cl | CF₃ | H | Cl |
| i-C₃H₇ | i-C₃H₇ | Cl | H | CF₃ | H | H |
| i-C₃H₇ | i-C₃H₇ | Cl | H | OCF₃ | H | H |
| i-C₃H₇ | i-C₃H₇ | Cl | H | OCF₃ | H | Cl |
| i-C₃H₇ | i-C₃H₇ | Cl | H | SCF₃ | H | H |
| i-C₃H₇ | i-C₃H₇ | Cl | H | SCF₃ | H | Cl |
| i-C₃H₇ | i-C₃H₇ | Cl | H | SOCF₃ | H | H |
| i-C₃H₇ | i-C₃H₇ | Cl | H | SOCF₃ | H | Cl |
| i-C₃H₇ | i-C₃H₇ | Cl | H | SO₂CF₃ | H | H |
| i-C₃H₇ | i-C₃H₇ | Cl | H | SO₂CF₃ | H | Cl |
| i-C₃H₇ | i-C₃H₇ | Cl | H | Br | H | Cl |
| t-C₄H₉ | H | Cl | H | CF₃ | H | Cl |
| t-C₄H₉ | H | Cl | Cl | CF₃ | H | Cl |
| t-C₄H₉ | H | Cl | H | CF₃ | H | H |
| t-C₄H₉ | H | Cl | H | OCF₃ | H | H |
| t-C₄H₉ | H | Cl | H | OCF₃ | H | Cl |

TABLE 1-continued

| R¹ | R² | R³ | R⁴ | R⁵ | R⁶ | R⁷ |
|---|---|---|---|---|---|---|
| t-C₄H₉ | H | Cl | H | SCF₃ | H | H |
| t-C₄H₉ | H | Cl | H | SCF₃ | H | Cl |
| t-C₄H₉ | H | Cl | H | SOCF₃ | H | Cl |
| t-C₄H₉ | H | Cl | H | SOCF₃ | H | H |
| t-C₄H₉ | H | Cl | H | SO₂CF₃ | H | H |
| t-C₄H₉ | H | Cl | H | SO₂CF₃ | H | Cl |
| t-C₄H₉ | H | Cl | H | Br | H | Cl |
| H | t-C₄H₉ | Cl | H | CF₃ | H | Cl |
| H | t-C₄H₉ | Cl | Cl | CF₃ | H | Cl |
| H | t-C₄H₉ | Cl | H | CF₃ | H | H |
| H | t-C₄H₉ | Cl | H | OCF₃ | H | H |
| H | t-C₄H₉ | Cl | H | OCF₃ | H | Cl |
| H | t-C₄H₉ | Cl | H | SCF₃ | H | H |
| H | t-C₄H₉ | Cl | H | SCF₃ | H | Cl |
| H | t-C₄H₉ | Cl | H | SOCF₃ | H | H |
| H | t-C₄H₉ | Cl | H | SOCF₃ | H | Cl |
| H | t-C₄H₉ | Cl | H | SO₂CF₃ | H | H |
| H | t-C₄H₉ | Cl | H | SO₂CF₃ | H | Cl |
| H | t-C₄H₉ | Cl | H | Br | H | Cl |
| t-C₄H₉ | t-C₄H₉ | Cl | H | CF₃ | H | Cl |
| t-C₄H₉ | t-C₄H₉ | Cl | Cl | CF₃ | H | Cl |
| t-C₄H₉ | t-C₄H₉ | Cl | H | CF₃ | H | H |
| t-C₄H₉ | t-C₄H₉ | Cl | H | OCF₃ | H | H |
| t-C₄H₉ | t-C₄H₉ | Cl | H | OCF₃ | H | Cl |
| t-C₄H₉ | t-C₄H₉ | Cl | H | SCF₃ | H | H |
| t-C₄H₉ | t-C₄H₉ | Cl | H | SCF₃ | H | Cl |
| t-C₄H₉ | t-C₄H₉ | Cl | H | SOCF₃ | H | H |
| t-C₄H₉ | t-C₄H₉ | Cl | H | SOCF₃ | H | Cl |
| t-C₄H₉ | t-C₄H₉ | Cl | H | SO₂CF₃ | H | H |
| t-C₄H₉ | t-C₄H₉ | Cl | H | SO₂CF₃ | H | Cl |
| t-C₄H₉ | t-C₄H₉ | Cl | H | Br | H | Cl |
| t-C₄H₉ | CH₃ | Cl | H | CF₃ | H | Cl |
| t-C₄H₉ | CH₃ | Cl | Cl | CF₃ | H | Cl |
| t-C₄H₉ | CH₃ | Cl | H | CF₃ | H | H |
| t-C₄H₉ | CH₃ | Cl | H | OCF₃ | H | H |
| t-C₄H₉ | CH₃ | Cl | H | OCF₃ | H | Cl |
| t-C₄H₉ | CH₃ | Cl | H | SCF₃ | H | H |
| t-C₄H₉ | CH₃ | Cl | H | SCF₃ | H | Cl |
| t-C₄H₉ | CH₃ | Cl | H | SOCF₃ | H | H |
| t-C₄H₉ | CH₃ | Cl | H | SOCF₃ | H | Cl |
| t-C₄H₉ | CH₃ | Cl | H | SO₂CF₃ | H | H |
| t-C₄H₉ | CH₃ | Cl | H | SO₂CF₃ | H | Cl |
| t-C₄H₉ | CH₃ | Cl | H | Br | H | Cl |
| CH₃ | t-C₄H₉ | Cl | H | CF₃ | H | Cl |
| CH₃ | t-C₄H₉ | Cl | Cl | CF₃ | H | Cl |
| CH₃ | t-C₄H₉ | Cl | H | CF₃ | H | H |
| CH₃ | t-C₄H₉ | Cl | H | OCF₃ | H | H |
| CH₃ | t-C₄H₉ | Cl | H | OCF₃ | H | Cl |
| CH₃ | t-C₄H₉ | Cl | H | SCF₃ | H | H |
| CH₃ | t-C₄H₉ | Cl | H | SCF₃ | H | Cl |
| CH₃ | t-C₄H₉ | Cl | H | SOCF₃ | H | H |
| CH₃ | t-C₄H₉ | Cl | H | SOCF₃ | H | Cl |
| CF₃ | t-C₄H₉ | Cl | H | SO₂CF₃ | H | H |
| CH₃ | t-C₄H₉ | Cl | H | SO₂CF₃ | H | Cl |
| CH₃ | t-C₄H₉ | Cl | H | Br | H | Cl |
| F₃C— | H | Cl | H | CF₃ | H | Cl |
| F₃C— | H | Cl | Cl | CF₃ | H | Cl |
| F₃C— | H | Cl | H | CF₃ | H | H |
| F₃C— | H | Cl | H | OCF₃ | H | H |
| F₃C— | H | Cl | H | OCF₃ | H | Cl |
| F₃C— | H | Cl | H | SCF₃ | H | H |
| F₃C— | H | Cl | H | SCF₃ | H | Cl |
| F₃C— | H | Cl | H | SOCF₃ | H | H |
| F₃C— | H | Cl | H | SOCF₃ | H | Cl |
| F₃C— | H | Cl | H | SO₂CF₃ | H | H |
| F₃C— | H | Cl | H | SO₂CF₃ | H | Cl |
| F₃C— | H | Cl | H | Br | H | Cl |
| H | F₃C— | Cl | H | CF₃ | H | Cl |
| H | F₃C— | Cl | Cl | CF₃ | H | Cl |
| H | F₃C— | Cl | H | CF₃ | H | H |
| H | F₃C— | Cl | H | OCF₃ | H | H |
| H | F₃C— | Cl | H | OCF₃ | H | Cl |
| H | F₃C— | Cl | H | SCF₃ | H | Cl |
| H | F₃C— | Cl | H | SCF₃ | H | H |
| H | F₃C— | Cl | H | SOCF₃ | H | H |
| H | F₃C— | Cl | H | SOCF₃ | H | Cl |
| H | F₃C— | Cl | H | SO₂CF₃ | H | H |
| H | F₃C— | Cl | H | SO₂CF₃ | H | Cl |
| F₃C— | CH₃ | Cl | H | CF₃ | H | H |
| F₃C— | CH₃ | Cl | H | CF₃ | H | Cl |
| F₃C— | CH₃ | Cl | H | Br | H | Cl |

TABLE 1-continued

| R¹ | R² | R³ | R⁴ | R⁵ | R⁶ | R⁷ |
|---|---|---|---|---|---|---|
| F₃C— | F₃C— | Cl | H | CF₃ | H | Cl |
| F₃C— | F₃C— | Cl | Cl | CF₃ | H | Cl |
| F₃C— | F₃C— | Cl | H | CF₃ | H | H |
| F₃C— | F₃C— | Cl | H | OCF₃ | H | H |
| F₃C— | F₃C— | Cl | H | OCF₃ | H | Cl |
| F₃C— | F₃C— | Cl | H | SCF₃ | H | H |
| F₃C— | F₃C— | Cl | H | SCF₃ | H | Cl |
| F₃C— | F₃C— | Cl | H | SOCF₃ | H | H |
| F₃C— | F₃C— | Cl | H | SOCF₃ | H | Cl |
| F₃C— | F₃C— | Cl | H | SO₂CF₃ | H | H |
| F₃C— | F₃C— | Cl | H | SO₂CF₃ | H | Cl |
| F₃C— | F₃C— | Cl | H | Br | H | Cl |
| H₃COCH₂— | H | Cl | H | CF₃ | H | Cl |
| H₃COCH₂— | H | Cl | Cl | CF₃ | H | Cl |
| H₃COCH₂— | H | Cl | H | CF₃ | H | H |
| H₃COCH₂— | H | Cl | H | OCF₃ | H | H |
| H₃COCH₂— | H | Cl | H | OCF₃ | H | Cl |
| H₃COCH₂— | H | Cl | H | SCF₃ | H | H |
| H₃COCH₂— | H | Cl | H | SCF₃ | H | Cl |
| H₃COCH₂— | H | Cl | H | SOCF₃ | H | H |
| H₃COCH₂— | H | Cl | H | SOCF₃ | H | Cl |
| H₃COCH₂— | H | Cl | H | SO₂CF₃ | H | H |
| H₃COCH₂— | H | Cl | H | SO₂CF₃ | H | Cl |
| H₃COCH₂— | H | Cl | H | Br | H | H |
| H | H₃COCH₂— | Cl | H | CF₃ | H | Cl |
| H | H₃COCH₂— | Cl | Cl | CF₃ | H | Cl |
| H | H₃COCH₂— | Cl | H | CF₃ | H | H |
| H | H₃COCH₂— | Cl | H | OCF₃ | H | H |
| H | H₃COCH₂— | Cl | H | OCF₃ | H | Cl |
| H | H₃COCH₂— | Cl | H | SCF₃ | H | H |
| H | H₃COCH₂— | Cl | H | SCF₃ | H | Cl |
| H | H₃COCH₂— | Cl | H | SOCF₃ | H | H |
| H | H₃COCH₂— | Cl | H | SOCF₃ | H | Cl |
| H | H₃COCH₂— | Cl | H | SO₂CF₃ | H | H |
| H | H₃COCH₂— | Cl | H | SO₂CF₃ | H | Cl |
| H | H₃COCH₂— | Cl | H | Br | H | Cl |
| H | HOCH₂— | Cl | H | CF₃ | H | Cl |
| H | HOCH₂— | Cl | Cl | CF₃ | H | Cl |
| H | HOCH₂— | Cl | H | CF₃ | H | H |
| H | HOCH₂— | Cl | H | OCF₃ | H | H |
| H | HOCH₂— | Cl | H | OCF₃ | H | Cl |
| H | HOCH₂— | Cl | H | SCF₃ | H | H |
| H | HOCH₂— | Cl | H | SCF₃ | H | Cl |
| H | HOCH₂— | Cl | H | SOCF₃ | H | H |
| H | HOCH₂— | Cl | H | SOCF₃ | H | Cl |
| H | HOCH₂— | Cl | H | SO₂CF₃ | H | H |
| H | HOCH₂— | Cl | H | SO₂CF₃ | H | Cl |
| H | HOCH₂— | Cl | H | Br | H | Cl |
| HOCH₂— | H | Cl | H | CF₃ | H | Cl |
| HOCH₂— | H | Cl | Cl | CF₃ | H | Cl |
| HOCH₂— | H | Cl | H | CF₃ | H | H |
| HOCH₂— | H | Cl | H | OCF₃ | H | H |
| HOCH₂— | H | Cl | H | OCF₃ | H | Cl |
| HOCH₂— | H | Cl | H | SCF₃ | H | H |
| HOCH₂— | H | Cl | H | SCF₃ | H | Cl |
| HOCH₂— | H | Cl | H | SOCF₃ | H | H |
| HOCH₂— | H | Cl | H | SOCF₃ | H | Cl |
| HOCH₂— | H | Cl | H | SO₂CF₃ | H | H |
| HOCH₂— | H | Cl | H | SO₂CF₃ | H | Cl |
| HOCH₂— | H | Cl | H | Br | H | Cl |
| 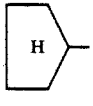 | H | Cl | H | CF₃ | H | Cl |
| 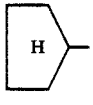 | H | Cl | Cl | CF₃ | H | Cl |
| 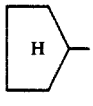 | H | Cl | H | CF₃ | H | H |

TABLE 1-continued
| R¹ | R² | R³ | R⁴ | R⁵ | R⁶ | R⁷ |
|---|---|---|---|---|---|---|
|  | H | Cl | H | OCF₃ | H | H |
|  | H | Cl | H | OCF₃ | H | Cl |
|  | H | Cl | H | SCF₃ | H | H |
|  | H | Cl | H | SCF₃ | H | Cl |
|  | H | Cl | H | SOCF₃ | H | H |
|  | H | Cl | H | SOCF₃ | H | Cl |
|  | H | Cl | H | SO₂CF₃ | H | H |
|  | H | Cl | H | SO₂CF₃ | H | H |
|  | H | Cl | H | Br | H | Cl |
| H |  | Cl | H | CF₃ | H | Cl |
| H |  | Cl | Cl | CF₃ | H | Cl |
| H |  | Cl | H | CF₃ | H | H |
| H |  | Cl | H | OCF₃ | H | H |

TABLE 1-continued

| R¹ | R² | R³ | R⁴ | R⁵ | R⁶ | R⁷ |
|---|---|---|---|---|---|---|
| H | ⟨H⟩ | Cl | H | OCF₃ | H | Cl |
| H | ⟨H⟩ | Cl | H | SCF₃ | H | H |
| H | ⟨H⟩ | Cl | H | SCF₃ | H | Cl |
| H | ⟨H⟩ | Cl | H | SOCF₃ | H | H |
| H | ⟨H⟩ | Cl | H | SOCF₃ | H | Cl |
| H | ⟨H⟩ | Cl | H | SO₂CF₃ | H | H |
| H | ⟨H⟩ | Cl | H | SO₂CF₃ | H | Cl |
| H | ⟨H⟩ | Cl | H | Br | H | Cl |

The 4-nitro-1-phenyl-pyrazoles of the formula (I) which can be used according to the invention are known in some cases (compare, for example, Bull. Soc. Chim. France 3727-3743 (1966); J. Chem. Soc. B, 211-214 (1968); J. Heterocycl. Chem. 7, 345-349 (1970); Farmaco Ed. Sci. 21, 883-891 (1966) and C.A. 66: 115640 p).

Compounds which are not yet known are 4-nitro-1-phenyl-pyrazoles of the formula (Ia)

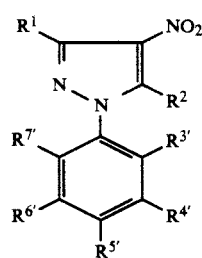

(Ia)

in which

R¹ and R² independently of one another represent hydrogen, alkyl, cycloalkyl, hydroxyalkyl, alkoxyalkyl, alkylthioalkyl or halogenoalkyl and R³', R⁴', R⁵', R⁶' and R⁷' each independently of one another represent hydrogen, halogen, cyano, nitro, alkyl, alkoxy, alkylthio, alkylsulphinyl, alkylsulphonyl or alkoxycarbonyl, or represent a radical —(X)$_n$—R⁸, wherein X represents oxygen, sulphur, sulphinyl or sulphonyl, n represents the number 0 or 1 and R⁸ represents halogenoalkyl, but wherein at least one of the radicals R³', R⁴', R⁵', R⁶' or R⁷' represents cyano, alkylthio, alkylsulphinyl, alkylsulphonyl, alkoxycarbonyl, or represents a radical —(X)$_n$—R⁸, or wherein at least three of the radicals R³', R⁴', R⁵', R⁶' or R⁷' represent identical or different halogen atoms, but in the case where R¹ and R² simultaneously represent hydrogen, at least one of the radicals R³', R⁴', R⁵', R⁶' or R⁷' is other than fluorine.

Preferred compounds of the formula (Ia) are those in which

R¹ and R² each independently of one another represent hydrogen, or represent in each case straight-chain or branched alkyl, hydroxyalkyl, alkoxyalkyl, alkylthioalkyl or halogenoalkyl with in each case up to 4 carbon atoms in the individual alkyl parts and, where appropriate, up to 9 identical or different halogen atoms, or represent cycloalkyl with 3 to 7 carbon atoms and $R^{3'}$, $R^{4'}$, $R^{5'}$, $R^{6'}$ and $R^{7'}$ each independently of one another represent hydrogen, fluorine, chlorine, bromine, iodine, cyano, nitro or in each case straight-chain or branched alkyl, alkoxy, alkylthio, alkylsulphinyl, alkylsulphonyl or alkoxycarbonyl with in each case up to 4 carbon atoms in the individual alkyl parts, or represent a radical $-(X)_n-R^8$, wherein X represents oxygen, sulphur, sulphinyl or sulphonyl,
n represents the number 0 or 1 and
$R^8$ represents straight-chain or branched halogenoalkyl with up to 4 carbon atoms and up to 9 identical or different halogen atoms,
but wherein
at least one of the radicals $R^{3'}$, $R^{4'}$, $R^{5'}$, $R^{6'}$ or $R^{7'}$ represents cyano, or represents alkylthio, alkylsulphinyl, alkylsulphonyl or alkoxycarbonyl with in each case 1 to 4 carbon atoms in the individual alkyl parts, or represents a radical $-(X)_n-R^8$,
or wherein at least three of the radicals $R^{3'}$, $R^{4'}$, $R^{5'}$, $R^{6'}$ or $R^{7'}$ represent identical or different halogen atoms, but in the case where $R^1$ and $R^2$ simultaneously represent hydrogen, at least one of the radicals $R^{3'}$, $R^{4'}$, $R^{5'}$, $R^{6'}$ or $R^{7'}$ is other than fluorine.

In formula (Ia), $R^1$, $R^2$, $R^{3'}$, $R^{4'}$, $R^{5'}$, $R^{6'}$ and $R^{7'}$ particularly preferably have those meanings which have been mentioned as particularly preferred for $R^1$, $R^2$, $R^3$, $R^4$, $R^5$, $R^6$ and $R^7$ in the description of the compounds of the formula (I), but
at least one of the radicals $R^{3'}$, $R^{4'}$, $R^{5'}$, $R^{6'}$ or $R^{7'}$ represents cyano, or represents alkylthio, alkylsulphinyl, alkylsulphonyl or alkoxycarbonyl with in each case 1 or 2 carbon atoms in the individual alkyl parts, or represent a radical $-(X)_n-R^8$, or at least three of the radicals $R^{3'}$, $R^{4'}$, $R^{5'}$, $R^{6'}$ or $R^{7'}$ represent identical or different halogen atoms, but in the case where $R^1$ and $R^2$ simultaneously represent hydrogen, at least one of the radicals $R^{3'}$, $R^{4'}$, $R^{5'}$, $R^{6'}$ or $R^{7'}$ is other than fluorine.

The 4-nitro-1-phenyl-pyrazoles of the formula (Ia) which are not yet known are obtained by a process in which 1-phenylpyrazoles of the formula (II).

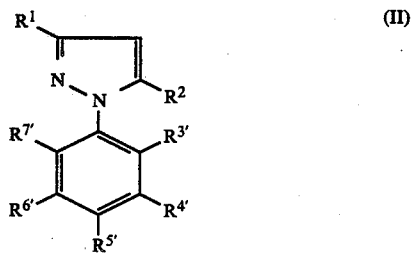

in which
$R^1$, $R^2$, $R^{3'}$, $R^{4'}$, $R^{5'}$, $R^{6'}$ and $R^{7'}$ have the abovementioned meaning,
are nitrated with nitric acid or nitric acid salts, if appropriate in the presence of a diluent and if appropriate in the presence of a catalyst.

The known 4-nitro-1-phenyl-pyrazoles of the formula (I) are also obtained by an analogous procedure.

If, for example, 1-(2,6-dichloro-4-trifluoromethylphenyl)pyrazole and nitric acid are used as the starting substances and sulphuric acid is used as the catalyst, the course of the reaction in the preparation process can be represented by the following equation:

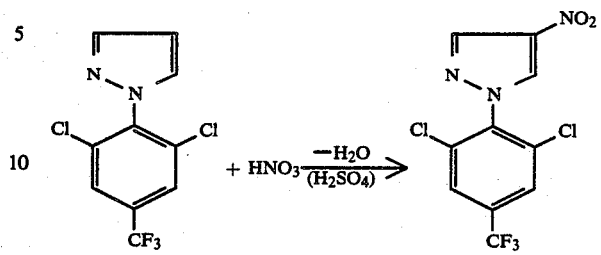

Formula (II) provides a general definition of the 1-phenylpyrazoles required as starting substances for carrying out the process according to the invention. In this formula (II), $R^1$ and $R^2$ preferably represent those radicals which have already been mentioned as preferred for these substituents in connection with the description of the substances of the formula (I) which can be used according to the invention.

$R^{3'}$, $R^{4'}$, $R^{5'}$, $R^{6'}$ and $R^{7'}$ preferably each represent hydrogen, fluorine, chlorine, bromine, cyano, nitro or in each case straight-chain or branched alkyl, alkoxy, alkylthio, alkylsulphinyl, alkylsulphonyl or alkoxycarbonyl with in each case up to 4 carbon atoms in the individual alkyl parts, or represent a radical $-(X)_n-R^8$, in particular hydrogen, fluorine, chlorine, cyano, nitro, methyl, ethyl, n- or i-propyl, methoxy, ethoxy, methylthio, methylsulphinyl, methylsulphonyl, methoxycarbonyl or ethoxycarbonyl, or represent a radical $-(X)_n-R^8$, wherein X represents oxygen, sulphur, sulphinyl or sulphonyl,
n represents the number 0 or 1 and
$R^8$ represents straight-chain or branched halogenoalkyl with up to 4 carbon atoms and up to 9 identical or different halogen atoms, in particular trifluoromethyl, trichloromethyl, dichlorofluoromethyl, difluorochloromethyl, dichloromethyl, chloromethyl, difluoromethyl, pentafluoroethyl, tetrafluoroethyl, trifluorochloroethyl, trifluoroethyl, difluorodichloroethyl, trifluorodichloroethyl or pentachloroethyl, but wherein
at least one of the radicals $R^{3'}$, $R^{4'}$, $R^{5'}$, $R^{6'}$ or $R^{7'}$ represents cyano, alkylthio, alkylsulphinyl, alkylsulphonyl or alkoxycarbonyl, or represents a radical $-(X)_n-R^8$ (X, n and $R^8$ having the above-mentioned meaning),
or wherein
at least three of the radicals $R^{3'}$, $R^{4'}$, $R^{5'}$, $R^{6'}$ and $R^{7'}$ represent identical or different halogen atoms, but in the case where $R^1$ and $R^2$ simultaneously represent hydrogen, at least one of the radicals $R^{3'}$, $R^{4'}$, $R^{5'}$, $R^{6'}$ or $R^{7'}$ is other than fluorine.

The 1-phenylpyrazoles of the formula (II) are known in some cases (compare, for example, J.Chem. Soc. Perkin Trans. 1, 982–984 (1980); and Tetrahedron Letters 925–928 (1976)).

They are obtained, for example, by a process in which 1,3-diketones of the formula (III)

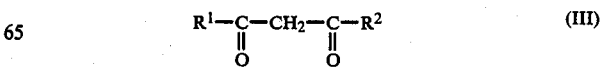

in which $R^1$ and $R^2$ have the abovementioned meaning, or derivatives of these diketones, such as, for example, enol ethers of the formula (IIIa)

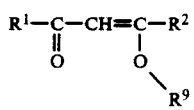 (IIIa)

in which
$R^1$ and $R^2$ have the abovementioned meaning and
$R^9$ represents alkyl, alkanoyl or aroyl, or ketals of the formulae (IIIb), (IIIc) or (IIId)

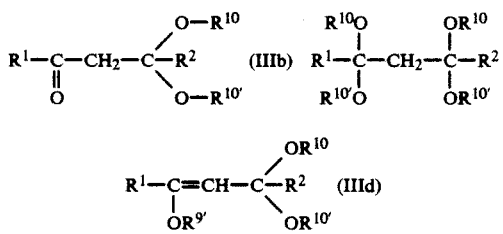

in which
$R^1$ and $R^2$ have the abovementioned meaning,
$R^{9'}$ represents alkyl and
$R^{10}$ and $R^{10'}$ each independently of one another represent alkyl, or together represent a divalent alkanediyl radical,
or enamines of the formula (IIIe)

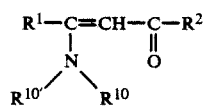 (IIIe)

in which
$R^1$, $R^2$, $R^{10}$ and $R^{10'}$ have the abovementioned meaning, or halides of the formula (IIIf)

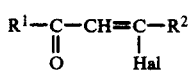 (IIIf)

in which
$R^1$ and $R^2$ have the abovementioned meaning and
Hal represents halogen,
are cyclized with phenylhydrazines of the formula (IV)

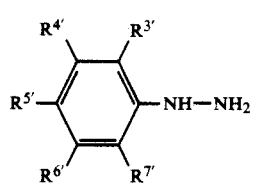 (IV)

in which
$R^{3'}$, $R^{4'}$, $R^{5'}$, $R^{6'}$ and $R^{7'}$ have the abovementioned meaning,
if appropriate in the presence of a diluent, such as, for example, ethylene glycol monoethyl ether or ethanol, at temperatures between $+50°$ C. and $+150°$ C.

Starting products of the formula (IIa)

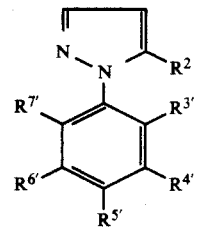 (IIa)

in which
$R^2$, $R^{3'}$, $R^{4'}$, $R^{5'}$, $R^{6'}$ and $R^{7'}$ have the above-mentioned meaning,
are alternatively obtained by reacting phenyl hydrazines of the formula (IV)

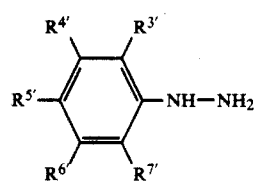 (IV)

in which
$R^{3'}$, $R^{4'}$, $R^{5'}$, $R^{6'}$ and $R^{7'}$ have the abovementioned meaning,
with acrylic ester derivatives of the formula (V)

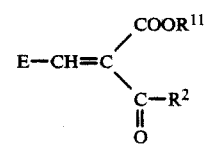 (V)

in which
$R^2$ has the abovementioned meaning,
$R^{11}$ represents alkyl, in particular methyl or ethyl and
E represents alkoxy, in particular methoxy or ethoxy, or dialkylamino, in particular dimethylamino, either initially in a first step, if appropriate in the presence of a diluent, such as for example ethanol or diethyl ether and, if appropriate, in the presence of a reaction auxiliary, such as for example hydrochloric acid, at temperatures between $-20°$ C. and $+20°$ C., to give the aryl hydrazine derivatives of the formula (VI)

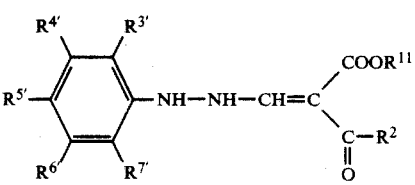 (VI)

in which
$R^2$, $R^{3'}$, $R^{4'}$, $R^{5'}$, $R^{6'}$, $R^{7'}$ and $R^{11}$ have the above-mentioned meaning,
and cyclizing these derivatives in a second step, if appropriate, in the presence of a diluent, such as for example ethanol, and if appropriate, in the presence of a catalyst, such as for example sulphuric acid, at temperatures between $+50°$ C. and $+150°$ C., or by direct cyclization in one reaction step without isolating the intermediate products of the formula (VI), if appropriate, in the presence of a diluent such as, for example, ethanol or ethylene glycol monoethyl ether, at temperatures between +50° C. and +150° C., and then hydrolyzing the 5-substituted pyrazole-4-carboxylic acid esters, thus obtainable, of the formula (VII)

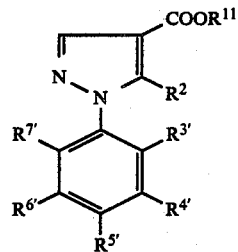
(VII)

in which
$R^2$, $R^{3'}$, $R^{4'}$, $R^{5'}$, $R^{6'}$, $R^{7'}$ and $R^{11}$ have the abovementioned meaning,
in a customary manner, for example with bases such as sodium hydroxide or with acids, such as hydrobromic acid, if appropriate, in the presence of a diluent such as for example ethanol or water, at temperatures between −20° C. and +100° C. and decarboxylating the 5-substituted pyrazole-4-carboxylic acids, thus obtainable of the formula (VIII),

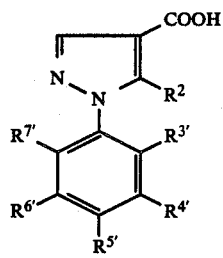
(VIII)

in which
$R^2$, $R^{3'}$, $R^{4'}$, $R^{5'}$, $R^{6'}$ and $R^{7'}$ have the above-mentioned meaning,
if appropriate, in the presence of a diluent such as, for example, ethanol or water, at temperatures between +100° C. and +200° C. The hydrolysis of the pyrazole-4-carboxylic acid esters of the formula (VII) and the subsequent decarboxylation of the pyrazole-4-carboxylic acids of the formula (VIII) can also be carried out in one reaction step in a so-called "one-pot process" without isolation of the pyrazole-4-carboxylic acids of the formula (VIII).

Starting products of the formula (IIb),

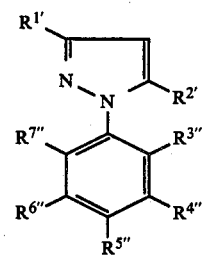
(IIb)

in which
$R^{1'}$ and $R^{2'}$ independently of one another each represent hydrogen, alkyl, cycloalkyl, hydroxyalkyl or halogenoalkyl and $R^{3''}$, $R^{4''}$, $R^{5''}$, $R^{6''}$ and $R^{7''}$ each independently of one another represent hydrogen, halogen, cyano, nitro, alkyl, alkoxy, alkylsulphinyl, alkylsulphonyl, alkoxycarbonyl or a radical —$(X')_n$—$R^8$, wherein
$X'$ represents oxygen, sulphinyl or sulphonyl,
n represents a number 0 or 1 and
$R^8$ represents halogenoalkyl,
wherein at least one of the radicals $R^{3''}$, $R^{4''}$, $R^{5''}$, $R^{6''}$ or $R^{7''}$ represents an alkylsulphinyl or an alkylsulphonyl or a halogenoalkylsulphinyl or a halogenoalkylsulphonyl radical,
are also obtained from compounds of the formula (IIc),

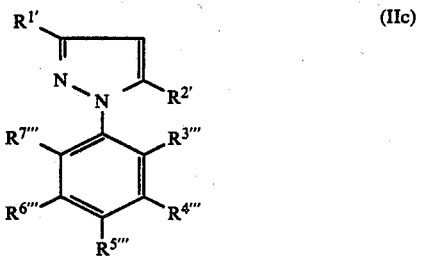
(IIc)

in which
$R^{1'}$ and $R^{2'}$ have the abovementioned meaning and
$R^{3'''}$, $R^{4'''}$, $R^{5'''}$, $R^{6'''}$ and $R^{7'''}$ each independently represent hydrogen, halogen, cyano, nitro, alkyl, alkoxy, alkylthio, alkoxycarbonyl or a radical —$(X'')_n$—$R^8$, wherein
$X''$ represents oxygen or sulphur,
n represents a number 0 or 1 and
$R^8$ represents halogenoalkyl,
wherein at least one of the radicals $R^{3'''}$, $R^{4'''}$, $R^{5'''}$, $R^{6'''}$ and $R^{7'''}$ represents an alkylthio or an halogenoalkylthio radical, by oxidation of the alkylthio or halogenoalkylthio group by generally known methods with the aid of customary oxidation reagents, such as for example hydrogen peroxide or m-chloroperbenzoic acid (cf. also the preparation examples).

The 1,3-diketones of the formula (III) and derivatives thereof of the formulae (IIIa) to (IIIf) and the acrylester derivatives of formula (V) are generally known compounds of organic chemistry (compare, for example, Chem. Ber. 59, 1282 (1926); Liebigs Ann. Chem. 452, 182 (1927); and J. Org. Chemistry 21, 97 (1956)).

The phenylhydrazines of the formula (IV) are known in most cases or can be prepared by a simple process analogous to known processes (compare, for example, Houben-Weyl, "Methoden der organischen Chemie" ("Methods of Organic Chemistry"), Volume X/2, page 203, Thieme Verlag Stuttgart 1967), for example by a procedure in which the known anilines of the formula (IX)

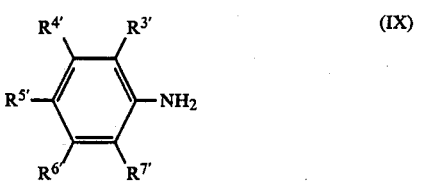
(IX)

in which $R^{3'}$, $R^{4'}$, $R^{5'}$, $R^{6'}$ and $R^{7'}$ have the abovementioned meaning,
are reacted with sodium nitrite in the presence of an acid, such as, for example, sulphuric acid, and then with tin-II chloride, also in the presence of an acid, such as, for example, hydrochloric acid, at temperatures between −20° C. and +80° C.

Possible diluents for carrying out the preparation process for the 4-nitro-1-phenyl-pyrazoles of the formula (Ia), which are not yet known, are all the solvents which can usually be employed for such nitration reactions. The nitric acid simultaneously employed as a reagent or a mixture thereof with catalyst acids, such as, for example, sulphuric acid, is preferably used in a corresponding excess as the diluent.

If appropriate, inert organic solvents, such as, for example, glacial acetic acid or chlorinated hydrocarbons, such as methylene chloride, chloroform or carbon tetrachloride, can also be used as diluents.

Possible catalysts or reaction auxiliaries for carrying out the preparation process are likewise the catalysts which are customary for such nitration reactions, such as, for example, sulphuric acid, iron-III chloride or other Lewis acids or acetic anhydride.

The reaction temperatures can be varied within a substantial range in carrying out the preparation process. In general, the reaction is carried out between −50° C. and +200° C., preferably between −20° C. and +150° C.

For carrying out the preparation process, in general 1.0 to 30.0 moles, preferably 1.0 to 20.0 moles, of nitric acid or nitric acid salt (preferably copper nitrate) and, if appropriate, 0.1 to 10 moles of catalyst or reaction auxiliary are employed per mole of 1-phenyl-pyrazole of the formula (II). The reaction is carried out and the reaction products of the formula (Ia) are worked up and isolated in the generally customary manner.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera:
Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera:
Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera:
Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristytis, Sagittaria, Eleocharis, Scirpus, Paspalum, Ischaemum, Sphenoclea, Dactyloctenium, Agrostis, Alopecurus and Apera.

Monocotyledon cultures of the genera:
Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds of the formula (I) which can be used according to the invention thereby also exhibit, in addition to a particularly good general herbicidal action, a clearly improved selectivity towards crop plants and can therefore be employed with particularly good success for selectively combating monocotyledon and dicotyledon weeds in monocotyledon and dicotyledon crops, such as, for example, cotton, soya and cereals.

When applied in appropriate amounts, the active compounds of the formula (I) according to the invention also have a fungicidal activity and can be used, for example, for combating rice spot disease (Pyricularia oryzae).

The active compounds which can be used according to the invention moreover have a favorable level of toxicity to warm-blooded animals and are suitable for combating animal pests, especially insects, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of Diplopoda, for example, *Blaniulus guttulatus.* From the order of the Chilopoda, for example, *Geophilus carpophagus* and *Scutigera spex.* From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blatella germanica, Acheta domesticus,* Gryllotalpa spp., *Locusta migratoria migratorioides, Melanoplus differntialis* and *Schistocerca gregaria.* From the order of Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Coleoptera, for example, *Anobium punctatum, Rhizopertha dominica, Bruchidius* obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis Atomaria spp., Oryzaephilus surinamensis, Anthonomus spp., Sitophilus spp., Otiorrhynhcus sulcatus, Cosmopolites sordidus, Ceuthorrhynchus assimilis, Hypera postica, Dermestes spp., Trogoderma spp., Anthrenus spp., Attagenus spp., Lyctus spp., Maligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica. From the order of the Hymenoptera, for example, Diprion spp., Hoplocampa spp., Lasius spp., Monomorium pharaonis and Vespa spp. From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyani, Ceratitis capitata, Dacus oleae and Tipula paludosa. From the order of the Siphonaptera, for example, Xenopsylla cheopis and Ceratophyllus spp. From the order of the Arachnida, for example, Scorpio maurus and Latrodectus mactans. From the order of the Homoptera, for example, Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp. From the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia Litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguells, Homona magnanima and Tortrix viridana.

The active compounds of the formula (I) which can be used according to the invention are thereby distinguished by a very good activity as soil insecticides and leaf insecticides.

In particular, however, the active compounds which can be used according to the invention can be employed with particularly good success when used against hygiene pests and pests of stored products, thus, for example, for combating the common grain weevil (Sitophilus granarius).

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

When employed as herbicides, the active compounds which can be used according to the invention, as such or in the form of their formulations, can also be employed, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea, for combating weeds in cereals; 4-amino-3-methyl-6-phenyl-1,2,4-triazin-5(4H)-one, for combating weeds in sugar beet, and 4-amino-6-(1,1-dimethyl-ethyl)-3-methylthio-1,2,4-triazin-5(4H)-one, for combating weeds in soy beans.

Mixtures with N,N-dimethyl-N'-(3-trifluoromethylphenyl)-urea, N,N-dimethyl-N'-(3-chloro-4-methylphenyl)-urea, N,N-dimethyl-N'-(4-isopropylphenyl)-urea, 4-amino-6-t-butyl-3-ethylthio-1,2,4-triazin-5(4H)-one, 2,4-dichlorophenoxyacetic acid, 2,4-dichlorophenoxypropionic acid, (2-methyl-4-chlorophenoxy)-acetic acid, (4-chloro-2-methylphenoxy)-propionic acid, chloroacetic acid N-(methoxymethyl)-2,6-diethylanilide, 2-ethyl-6-methyl-N-(1-methyl-2-methoxyethyl)-chloroacetanilide, 2,6-dinitro-4-trifluoromethyl-N,N-dipropylaniline, 2-benzyloxyethyl, trimethylsilylmethyl or 2,2-diethoxyethyl 2-[4-(3,5-dichloropyrid-2-yloxy)-phenoxy]-propionate, 2-[1-(ethoxamino)-butylidene]-5-(2-ethylthiopropyl)-1,3-cyclohexanedione; 2-chloro-N-(2,6-dimethylphenyl)-N-(1H-pyrazol-1-ylmethyl)-acetamide; N-methyl-2-(1,3-benzothiazol-2-yloxy)-acetanilide; S-ethyl N,N-di-n-propyl-thiocarbamate; exo-1-methyl-4-(1-methylethyl)-2-(2-methylphenylphenoxy)-7-oxabicyclo-[2,2,1]-heptane and 2-<4-[[3-chloro-5-trifluoromethyl]-2-pyridinyl]oxy]-phenoxy>-propionic acid or -propanoic acid ethyl ester are also possible. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds which can be used according to the invention can be employed as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds which can be used according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per hectare.

When used as insecticides, the active compounds which can be used according to the invention can also be present in their commercially available formulations and in the use forms, prepared from these-formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds which can be used according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The preparation and use of the active compounds which can be used according to the invention can be seen from the following examples.

PREPARATION EXAMPLES

Example 1

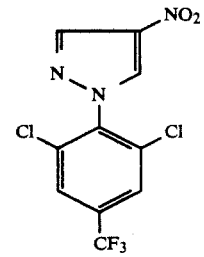

30 ml (0.714 mole) of 98 percent strength nitric acid are added to 31.5 g (0.112 mole) of 1-(2,6-dichloro-4-trifluoromethylphenyl)-pyrazole in 150 ml of 96 percent strength sulphuric acid at room temperature such that the temperature of the reaction mixture does not exceed 40° C. When the addition has ended, the mixture is stirred at 50° C. for 2 hours and then cooled to about 15° C. and poured carefully into about 1,000 g of ice. The precipitate is filtered off with suction, washed neutral with about 500 ml of water and dried at 50° C. in vacuo.

34.7 g (95% of theory) of 1-(2,6-dichloro-4-trifluoromethylphenyl)-4-nitropyrazole of melting point 91°–97° C. are obtained.

EXAMPLE 2

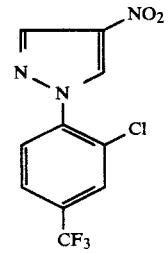

A solution of 6 g (0.025 mole) of 1-(2-chloro-4-trifluoromethylphenyl)-pyrazole in 22 ml of glacial acetic acid is added dropwise to a solution of 6.8 ml (0.15 mole) of 98 percent strength nitric acid in 22 ml of glacial acetic acid and 16 ml of acetic anhydride at 10° C. to 15° C., with stirring. When the addition has ended, the mixture is warmed slowly to 40° C. and stirred at this temperature for 15 hours. For working up, the reaction mixture is poured carefully into about 600 ml of ice-water and the precipitate which has separated out is filtered off with suction, rinsed with about 300 ml of water and dried in vacuo at 40° C. to 50° C.

6.1 g (85% of theory) of 1-(2-chloro-4-trifluoromethylphenyl)-4-nitro-pyrazole of melting point 106° C.–109° C. are thus obtained.

EXAMPLE 3

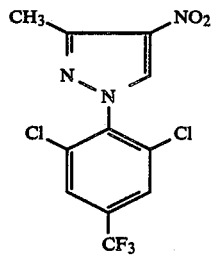

5.3 ml (0.12 mole) of 98% strength nitric acid are slowly added dropwise to a solution of 5.9 g (0.02 mole) of 1-(2,6-dichloro-4-trifluoromethylphenyl)-3-methyl-pyrazole in 28 ml of concentrated sulphuric acid at 20° C. When the addition has ended, the mixture is stirred at room temperature for 4 hours, poured onto ice-water and extracted with methylene chloride. The organic phase is washed with saturated sodium carbonate solution and water and dried over magnesium sulphate and the solvent is distilled off in vacuo.

5 g (73% of theory) of 1-(2,6-dichloro-4-trifluoromethylphenyl)-3-methyl-4-nitropyrazole of melting point 76° C.–82° C. containing about 6% of the 5-methyl isomer are obtained.

EXAMPLE 4

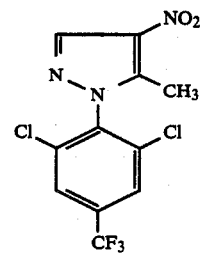

5 g (0.0147 mole) of 4-carboxyl-5-methyl-1-(2,6-dichloro-4-trifluoromethyl-phenyl)-pyrazole are dissolved in 36 ml of concentrated hydrochlorid acid. 3.8 ml (0.0394 mole) of 98% strength nitric acid are added dropwise, the mixture is heated for 1 hour to 120° C. and then left to cool. The reaction mixture is poured on ice water, extracted with methylene chloride, the methylene chloride phases are washed with saturated sodium hydrogen carbonate solution, dried over magnesium sulphate and concentrated in vacuo.

3.7 g (74% of theory) of 5-methyl-4-nitro-1-(2,6-dichloro-4-trifluoromethyl-phenyl)-pyrazole with a melting point of 91°–92° C. are obtained.

The following 4-nitro-1-phenylpyrazoles of the general formula (I) are obtained in a corresponding manner and in accordance with the general preparation statements:

TABLE 2

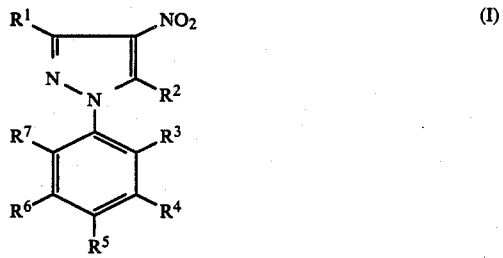

| Example | $R^1$ | $R^2$ | $R^3$ | $R^4$ | $R^5$ | $R^6$ | $R^7$ | Melting point/°C. |
|---|---|---|---|---|---|---|---|---|
| 5 | H | H | Cl | H | $F_3CS$— | H | Cl | 89 |
| 6 | H | H | Cl | H | $F_3C$—SO— | H | Cl | 140 |
| 7 | H | H | Cl | Cl | $F_3C$— | H | Cl | 92–94 |
| 8 | H | H | Cl | H | $F_3C$—$SO_2$— | H | Cl | 218–219 |
| 9 | H | H | Cl | H | $F_3C$—$SO_2$— | H | H | 84–85 |
| 10 | H | H | Cl | $NO_2$ | $F_3CS$— | H | Cl | 155–159 |
| 11 | H | H | Cl | $NO_2$ | $F_3C$— | H | Cl | 115–123 |
| 12 | H | H | Cl | Cl | Cl | H | H | 135–137 |
| 13 | $CH_3$ | $CH_3$ | Cl | H | $F_3C$— | H | Cl | 83 |
| 14 | H | H | H | H | $NO_2$ | H | H | 118–120 |
| 15 | H | H | Br | H | $F_3C$— | H | Br | 120–121 |
| 16 | H | H | Cl | $NO_2$ | H | H | Cl | 147–151 |
| 17 | H | H | F | F | $F_3C$— | F | F | 70–72 |
| 18 | H | H | Cl | F | $F_3C$— | F | Cl | 89–90 |
| 19 | H | $CH_3$ | Cl | H | $F_3C$— | H | H | $^1$HNMR*: 8,27 |
| 20 | H | n-$C_3H_7$ | Cl | H | $F_3C$— | H | Cl | 64–70 |
| 21 | H | n-$C_3H_7$ | Cl | Cl | $F_3C$— | H | Cl | [1]H—NMR*: 8,38 |
| 22 | t-$C_4H_9$ | H | Cl | H | $F_3C$— | H | Cl | 65–68 |
| 23 | H | $CH_3$ | Cl | $NO_2$ | Cl | H | Cl | 110 |
| 24 | H | n-$C_3H_7$ | Cl | $NO_2$ | Cl | H | Cl | 147 |

*The [1]H—NMR Spectra were recorded in $CDCl_3$ using trimethylsilane as the internal standard. The figures given are the chemical shifts in the form of the δ-value in ppm.

PREPARATION OF THE STARTING COMPOUNDS

Example II-1

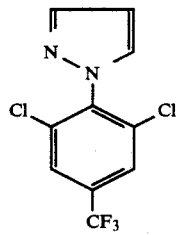

16.4 g (0.1 mole) of 1,1,3,3-tetramethoxypropane and 5.1 g (0.05 mole) of 96 percent strength sulphuric acid are added in succession to 24.3 g (0.1 mole) of 2,6-dichloro-4-trifluoromethylphenyl-hydrazine in 100 ml of ethanol and the mixture is heated at the reflux temperature for 2 hours. After the reaction mixture has cooled, it is neutralised with 5.3 g (0.05 mole) of sodium carbonate, stirred at room temperature for one hour and then concentrated in vacuo. The residue is taken up in 250 ml of water and extracted with 200 ml of methylene chloride. The organic phase is washed with water, dried over sodium sulphate and freed from the solvent in vacuo.

23.9 g (86.5% of theory) of 1-(2,6-dichloro-4-trifluoromethylphenyl)-pyrazole of melting point 83° C.–85° C. are obtained.

Example II-2

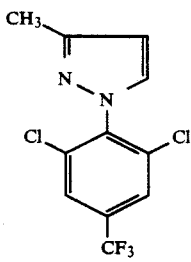

14 g (0.05 mole) of 2,6-dichloro-4-trifluoromethylphenylhydrazine and 6.6 g (0.05 mole) of 3-oxobutyraldehyde dimethyl acetal are dissolved in 100 ml of ethanol and the solution is stirred overnight at the reflux temperature. After the solution has cooled to room temperature, 1 ml of concentrated sulphuric acid is added and the mixture is stirred at 60° C. for about 5 hours and then concentrated in vacuo. The residue is taken up in methylene chloride, washed with saturated sodium bicarbonate solution and water and dried over magnesium sulphate and the solvent is distilled off in vacuo.

After the residue has been distilled at 100° C./0.06 mbar, 10 g (68% of theory) of 1-(2,6-dichloro-4-trifluoromethylphenyl)-3-methylpyrazole containing about 6% of the 5-methyl isomer are obtained.

Example II-3

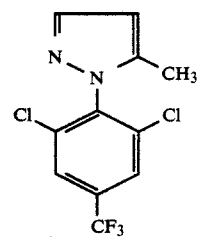

3.7 g (0.01 mole) of 4-ethoxycarbonyl-5-methyl-1-(2,6-dichloro-4-trifluoromethyl-phenyl)-pyrazole are heated in 40 ml of hydrobromic acid at 120°–125° C. for 48 hours, the ethanol forming being simultaneously distilled off. Then the excess hydrobromic acid is distilled off, the residue is taken up in methylene chloride and washed with saturated sodium hydrogen carbonate solution. The organic phase is dried over magnesium sulphate and concentrated in vacuo.

2.0 g (67% of theory) of 5-methyl-1-(2,6-dichloro-4-trifluoromethyl-phenyl)-pyrazole with a melting point of 78°–84° C. are obtained.

Example II-4

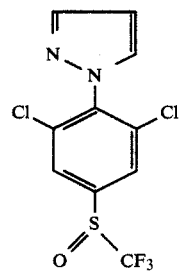

34.8 g (0.182 mole) of 90% strength m-chloroperbenzoic acid are added to 51.7 g (0.165 mole) of 1-(2,6-dichloro-4-trifluoromethylthiophenyl)-pyrazole in 300 ml of dichloromethane and the mixture is stirred for 18 hours at room temperature. In order to work up the reaction mixture it is filtered, the filtrate is washed successively with aqueous sodium hydrogen carbonate solution, sodium thiosulphate solution and sodium chloride solution and purified chromatographically over a silica gel column (mobile solvent: dichloromethane).

20.6 g (54% of theory) of 1-(2,6-dichloro-4-trifluoromethylsulphinyl-phenyl)-pyrazole with a melting point of 86°–91° C. are obtained (in addition to 15.6 g of non-reacted starting compound).

The following 1-phenyl-pyrazoles of the general formula (II) are prepared in a corresponding manner and according to the general description of the preparation:

TABLE 3

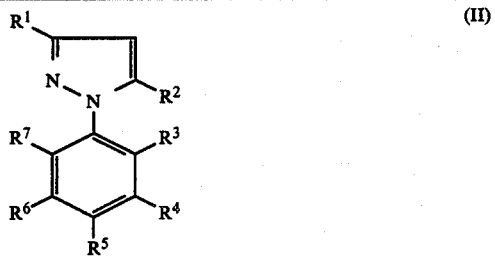

| Example | R¹ | R² | R³ | R⁴ | R⁵ | R⁶ | R⁷ | Melting point/°C. |
|---|---|---|---|---|---|---|---|---|
| II-5 | H | H | Cl | Cl | $F_3C-$ | H | Cl | 49–52 |
| II-6 | H | H | Cl | H | $F_3C-$ | H | H | $^1H-NMR^*$: Pyrazole H-3: 7,97 Pyrazole H-4: 6,46 |
| II-7 | H | H | Cl | H | $F_3C-SO_2-$ | H | H | 69–70 |
| II-8 | H | H | Cl | H | $F_3C-SO_2-$ | H | Cl | 113–115 |
| II-9 | H | H | Cl | H | $F_3CS-$ | H | Cl | $^1H-NMR^*$: Pyrazole H-3: 7,81 Pyrazole H-4: 6,51 |
| II-10 | $CH_3$ | $CH_3$ | Cl | H | $F_3C-$ | H | Cl | 80–81 |
| II-11 | H | $CH_3$ | Cl | H | $F_3C-$ | H | H | 45–47 |
| II-12 | H | $CH_3$ | Cl | H | $F_3C-SO_2-$ | H | H | 99–100 |
| II-13 | H | $n-C_3H_7$ | Cl | H | $F_3C-SO_2-$ | H | H | 66–67 |
| II-14 | H | $CF_3$ | $NO_2$ | H | $NO_2$ | H | H | 166 |
| II-15 | H | H | Br | H | $F_3C-$ | H | Br | 116–120 |

*The $^1H-NMR$ spectra were recorded in $CDCl_3$ using trimethylsilane as the internal standard. The figures given are the chemical shifts in the form of the δ-value in ppm.

Example VIII-1

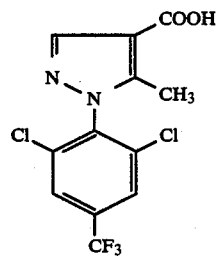

8.7 g (0.0237 mole) of 4-ethoxycarbonyl-5-methyl-1-(2,6-dichloro-4-trifluoromethyl-phenyl)-pyrazole are dissolved in a solution of 50 ml of ethanol, 1.5 g (0.0375 mole) of sodium hydroxide and 25 ml of water and stirred at room temperature for 48 hours. The reaction mixture is washed with methylene chloride and the alkaline phase is acidified with 2N hydrochloric acid with ice cooling. Then extraction with methylene chloride is carried out, the methylene chloride phase is dried over magnesium sulphate and concentrated in vacuo.

8 g (100% of theory) of 4-carboxy-5-methyl-1-(2,6-dichloro-4-trifluoromethyl-phenyl)-pyrazole with a melting point of 187°–189° C. are obtained.

The following compounds are obtained in a corresponding manner:

| Example | | Melting point: |
|---|---|---|
| VIII-2: | 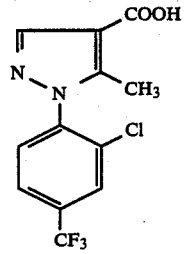 | 161–162° C. |
| VIII-3: | 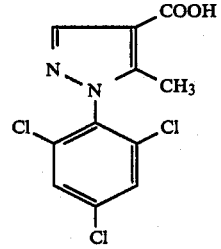 | 168–173° C. |

| Example | | Melting point: |
|---|---|---|
| VIII-4: | pyrazole with COOH, CH₃, N-N, phenyl (2,6-diCl, 4-CF₃) | 175–180° C. |
| VIII-5: | pyrazole with COOH, CH₂—CH₂—CH₃, N-N, phenyl (2,6-diCl, 4-CF₃) | 198°–200° C. |
| VIII-6: | pyrazole with COOH, CH₂—CH₂—CH₃, N-N, phenyl (2,6-diCl, 4-CF₃) | 158°–161° C. |
| VIII-7: | pyrazole with COOH, CH₂—CH₂—CH₃, N-N, phenyl (2,3,6-triCl, 4-CF₃) | 185°–190° C. |
| VII-1: | pyrazole with COOC₂H₅, CH₃, N-N, phenyl (2,6-diCl, 4-CF₃) | |

5 g (0.013 mole) of N-[2-ethoxycarbonyl-2-acetyl-vinyl]-N'-(2,6-dichloro-4-trifluoromethyl-phenyl)-hydrazine are dissolved in 50 ml of ethanol, 1 ml of concentrated sulphuric acid is added and the mixture is heated for 1 hour under reflux. The reaction mixture is concentrated in vacuo, taken up in methylene chloride, washed with saturated sodium hydrogen carbonate solution, the methylene chloride phase is dried over magnesium sulphate and concentrated in vacuo. 4.1 g (86% of theory) of 4-ethoxycarbonyl-5-methyl-1-(2,6-dichloro-4-trifluoromethyl-phenyl)-pyrazole with a melting point of 61°–62° C. are obtained.

The following compounds are obtained in a corresponding manner:

Example VII-2
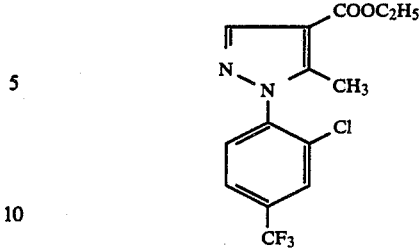
Melting point 69°–70° C.
| Example | | Melting point |
|---|---|---|
| VII-3 | (pyrazole-COOC$_2$H$_5$, N-aryl = 2-Cl, 4-CF$_3$-phenyl) | 160°–161° C. |
| VII-4 | (pyrazole-COOC$_2$H$_5$, 5-CH$_3$, N-aryl = 2,4,6-trichlorophenyl) | 101°–104° C. |
| VII-5 | (pyrazole-COOC$_2$H$_5$, 5-CH$_3$, N-aryl = 2,3,6-trichloro-4-CF$_3$-phenyl) | $^1$H—NMR: 8,17 |
| VII-6 | (pyrazole-COOC$_2$H$_5$, 5-CH$_3$, N-aryl = 2-Cl, 4-SO$_2$CF$_3$-phenyl) | 124°–125° C. |
| VII-7 | (pyrazole-COOC$_2$H$_5$, 5-CH$_2$CH$_2$CH$_3$, N-aryl = 2,4,6-trichlorophenyl) | 42°–46° C. |

-continued

| Example | | Melting point |
|---|---|---|
| VII-8 | 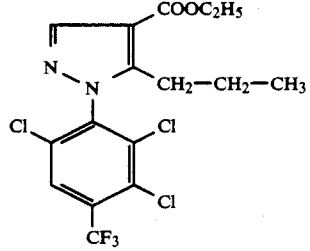 | 58°–60° C. |
| VII-9 | 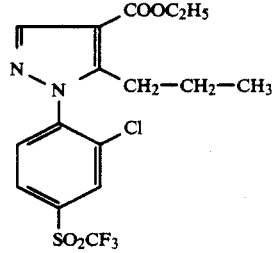 | 104°–105° C. |
| VII-10 | 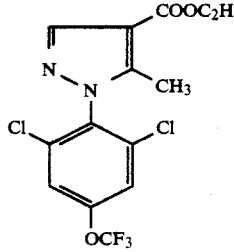 | 55°–65° C. |
| VII-11 | 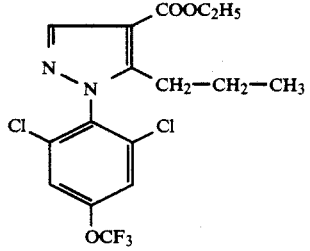 | $^1$H—NMR: 8,15 |
| VII-12 | 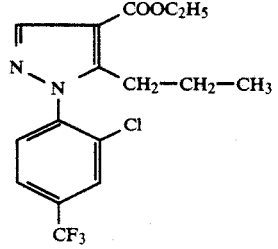 | 59°–64° C. |
| VI-1 | 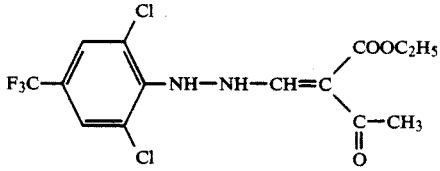 | |

12.25 g (0.05 mole) of 2,6-dichloro-4-trifluoromethylphenyl hydrazine in 25 ml of diethyl ether are added to a solution of 9.3 g (0.5 mole) of ethyl ethoxymethylene acetoacetate in 50 ml of diethyl ether dropwise with stirring, at 0° C. When the addition has ended the mixture is stirred for a further hour at room temperature and then concentrated in vacuo.

19 g (100% of theory) of N-[2-ethoxycarbonyl-2-acetyl-vinyl]-N'-(2,6-dichloro-4-trifluoromethylphenyl)hydrazine with a melting point of 75°–76° C. are obtained.

USE EXAMPLES

The compounds shown below were employed as comparison compounds in the following use examples:

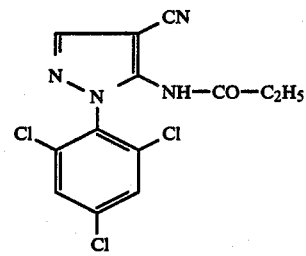

(A)

4-Cyano-5-propionylamino-1-(2,4,6-trichlorophenyl)-pyrazole (known from DE-OS (German Published Specification) No. 3,226,513)

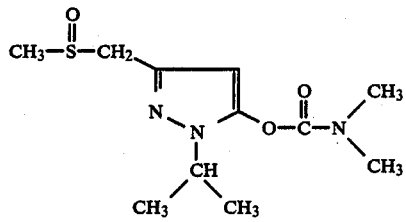

(B)

5-Dimethylaminocarbonyloxy-1-isopropyl-3-methylsulphinylmethylpyrazole (known from DE-OS (German Published Specification) No. 2,819,932)

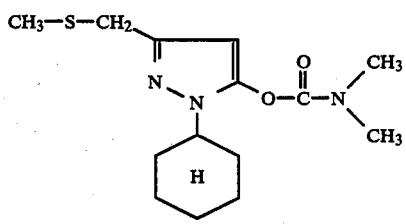

(C)

1-Cyclohexyl-5-dimethylaminocarbonyloxy-3-methylthiomethylpyrazole (known from DE-OS (German Published Specification) No. 2,839,270).

EXAMPLE A

Pre-emergence test

| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

| 0% = no action (like untreated control) |
| 100% = total destruction |

In this test, for example, a clear superiority both in activity and in selectivity towards useful plants in comparison with the prior art is shown by the compounds according to preparation Examples (1) and (7).

EXAMPLE B

| Test insects: | *Sitophilus granarius* |
| Number of test insects: | 25 |
| Solvent: | Acetone |

2 parts by weight of active compound are taken up in 1,000 parts by volume of solvent. The solution thus obtained is diluted with further solvent to the desired concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m² of filterpaper varies, depending on the concentration of the active compound solution. The stated number of test insects is then introduced into the Petri dish, and the dish is covered with a glass lid.

The condition of the test insects is checked 3 days after the experiments have been set up. The destruction in % is determined. 100% means that all the test insects have been killed; 0% means that none of the test insects have been killed.

In this test, for example, the following compound from the preparation examples exhibits a superior action compared with the prior art: (1)

It is understood that the specification and examples are illustrative but not limitative of the present invention and that other embodiments within the spirit and scope of the invention will suggest themselves to those skilled in the art.

What is claimed is:

1. A method of combating unwanted vegetation which comprises applying to such vegetation or to a locus from which it is desired to exclude such vegetation a herbicidally effective amount of at least one 4-nitro-1-phenyl-pyrazole of the formula

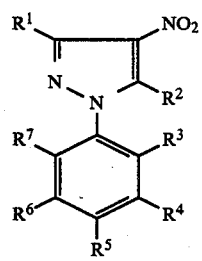

in which
$R^1$ and $R^2$ each independently is hydrogen, or alkyl, hydroxyalkyl, alkoxyalkyl, alkylthioalkyl or halogenoalkyl with in each case up to 4 carbon atoms in the individual alkyl parts and, where appropriate, up to 9 halogen atoms, or cycloalkyl with 3 to 7 carbon atoms, $R^3$, $R^4$, $R^5$, $R^6$ and $R^7$ each independently is hydrogen, halogen, cyano, nitro, or alkyl, alkoxy, alkylthio, alkylsulphinyl, alkylsulphonyl or alkoxycarbonyl with in each case up to 4 carbon atoms in the individual alkyl parts, or —$(X)_n$—$R^8$, X is oxygen, sulphur, sulphinyl or sulphonyl, n is 0 or 1, and $R^8$ is halogenoalkyl with up to 4 carbon atoms and and up to 9 halogen atoms.

2. A method according to claim 1, in which $R^1$ and $R^2$ each independently is hydrogen, methyl, ethyl, n- or i-propyl, n-, i-, s- or t-butyl, cyclohexyl, hydroxymethyl, methoxymethyl, methylthiomethyl, trifluoromethyl or trichloromethyl, and $R^3$, $R^4$, $R^5$, $R^6$ and $R^7$ each independently is hydrogen, fluorine, chlorine, bromine, iodine, cyano, nitro, methyl, ethyl, n- or i-propyl, methoxy, ethoxy, methylthio, methylsulphinyl, methylxulphonyl, methoxycarbonyl, ethoxycarbonyl, or —$(X)_n$—$R^8$, and $R^8$ is trifluoromethyl, trichloromethyl, dichlorofluoromethyl, difluorochloromethyl, dichloromethyl, chloromethyl, difluoromethyl, pentafluoroethyl, tetrafluoroethyl, trifluorochloroethyl, trifluoroethyl, difluorodichloroethyl, trifluorochloroethyl or pentachloroethyl.

3. A method according to claim 1, wherein such pyrazole is 1-(2,6-dichloro-4-trifluoromethylphenyl)-4-nitropyrazole of the formula

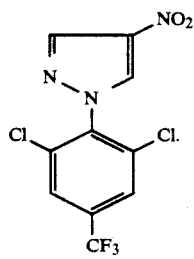

4. A method according to claim 1, wherein such pyrazole is 1-(2,6-dichloro-4-trifluoromethyl-sulphinyl-phenyl)-4-nitropyrazole of the formula

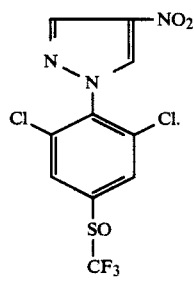

5. A method according to claim 1, wherein such pyrazole is 1-(2,3,6-trichloro-4-trifluoromethylphenyl)-4-nitropyrazole of the formula

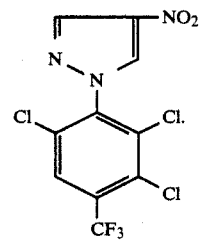

6. A method according to claim 1, wherein such pyrazole is 1-(2,6-dichloro-4-trifluoromethyl-sulphonyl-phenyl)-4-nitropyrazole of the formula

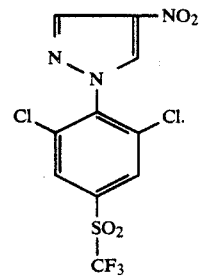

7. A method according to claim 1, wherein such pyrazole is 1-(2,3,4-trichlorophenyl)-4-nitropyrazole of the formula

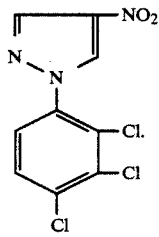

8. A 4-nitro-1-phenyl-pyrazole of the formula

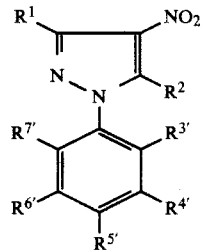

in which $R^1$ and $R^2$ each independently is hydrogen, or alkyl, hydroxyalkyl, alkoxyalkyl, alkylthioalkyl or halogenoalkyl with in each case up to 4 carbon atoms in the individual alkyl parts and, where appropriate, up to 9 halogen atoms, or cycloalkyl with 3 to 7 carbon atoms, $R^3$, $R^4$, $R^5$, $R^6$ and $R^7$ each independently is hydrogen, halogen, cyano, nitro, or alkyl, alkoxy, alkylthio, alkylsulphinyl, alkylsulphonyl or alkoxycarbonyl with in each case up to 4 carbon atoms in the individual alkyl parts, or —$(X)_n$—$R^8$, X is oxygen, sulphur, sulphinyl or sulphonyl, n is 0 or 1, and R⁸ is halogenoalkyl with up to 4 carbon atoms and and up to 9 halogen atoms.

but wherein at least one of the radicals R³', R⁴', R⁵', R⁶' or R⁷' is cyano, or alkylthio, alkylsulphinyl, alkylsulphonyl, alkoxycarbonyl with in each case 1 to 4 carbon atoms in the individual alkyl parts, or —(X)$_n$—R⁸, or wherein at least three of the radicals R³', R⁴', R⁵', R⁶' or R⁷' are halogen atoms, but in the case where R¹ and R² simultaneously are hydrogen, at least one of the radicals R³', R⁴', R⁵', R⁶' or R⁷' is other than fluorine.

9. A pyrazole according to claim 8, wherein such pyrazole is 1-(2,6-dichloro-4-trifluoromethyl-sulphinyl-phenyl)-3-methyl-4-nitropyrazole of the formula

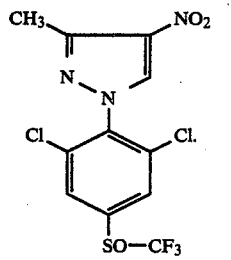

10. A pyrazole according to claim 8, wherein such pyrazole is 1-(2,6-dichloro-4-trifluoromethyl-sulphinyl-phenyl-4-nitropyrazole of the formula

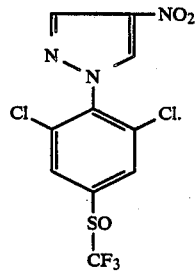

11. A pyrazole according to claim 8, wherein such pyrazole is 1-(2,3,6-trichloro-4-trifluoromethylphenyl)-4-nitropyrazole of the formula

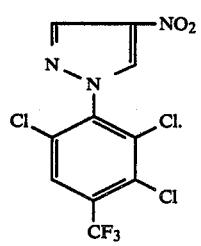

12. A pyrazole according to claim 8, wherein such pyrazole is 1-(2,6-dichloro-4-trifluoromethyl-sulphonyl-phenyl)-4-nitropyrazole of the formula

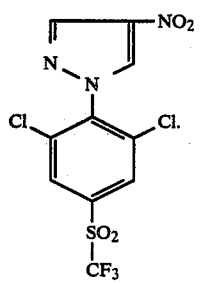

13. A pyrazole according to claim 8, wherein such pyrazole is 1-(2,3,4-trichlorophenyl)-4-nitropyrazole of the formula

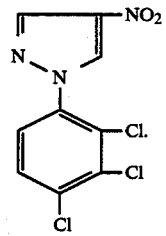

14. A herbicidal composition comprising a herbicidally effective amount of a compound according to claim 8 and a diluent.

15. A composition according to claim 14, wherein such compound is
1-(2,6-dichloro-4-trifluoromethyl-sulphinyl-phenyl)-3-methyl-4-nitropyrazole,
1-(2,3,6-trichloro-4-trifluoromethylphenyl)-4-nitropyrazole,
1-(2,6-dichloro-4-trifluoromethyl-sulphinyl-phenyl)-4-nitropyrazole,
1-(2,6-dichloro-4-trifluoromethyl-sulphonylphenyl)-4-nitropyrazole or
1-(2,3,4-trichlorophenyl)-4-nitropyrazole.

* * * * *

UNITED STATES PATENT AND TRADEMARK OFFICE
CERTIFICATE OF CORRECTION

PATENT NO. : 4,746,354

DATED : May 24, 1988

INVENTOR(S) : Reinhold Gehring, et al.

It is certified that error appears in the above-identified patent and that said Letters Patent is hereby corrected as shown below:

Col. 13, line 51 under "$R^5$"   Delete "$SO_{22}CF_3$" and substitute --$SO_2CF_3$--

Col. 15, line 29, from bottom under "$R^1$"   Delete "$CF_3$" and substitute --$CH_3$--

Col. 31, line 22   Correct spelling of --hyoscyami--

Col. 31, line 45   Correct --litura--

Col. 31, line 50   Correct spelling of --ambiguella--

Col. 33, line 23   Delete "propionic" and substitute --propanoic--

Col. 41, Example "VIII-6:"   Bottom of formula delete "$CF_3$" and substitute --Cl--

Signed and Sealed this

Sixth Day of December, 1988

Attest:

DONALD J. QUIGG

Attesting Officer

Commissioner of Patents and Trademarks